(12) United States Patent
Mathur et al.

(10) Patent No.: US 10,233,415 B1
(45) Date of Patent: Mar. 19, 2019

(54) MICROFLUIDICS CELL CULTURE DEVICE

(71) Applicant: The Regents of the University of California, Oakland, CA (US)

(72) Inventors: Anurag Mathur, Berkeley, CA (US); Peter Loskill, Berkeley, CA (US); Luke P. Lee, Orinda, CA (US); Kevin E. Healy, Moraga, CA (US); Soongweon Hong, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 495 days.

(21) Appl. No.: 14/906,492

(22) PCT Filed: Jul. 21, 2014

(86) PCT No.: PCT/US2014/047482
§ 371 (c)(1),
(2) Date: Jan. 20, 2016

(87) PCT Pub. No.: WO2015/013210
PCT Pub. Date: Jan. 29, 2015

Related U.S. Application Data

(60) Provisional application No. 61/856,795, filed on Jul. 22, 2013.

(51) Int. Cl.
*C12M 3/00* (2006.01)
*G01N 33/48* (2006.01)
*G01N 33/50* (2006.01)
*C12M 3/06* (2006.01)
*C12M 1/26* (2006.01)
*C12M 1/34* (2006.01)
*G01N 33/483* (2006.01)

(52) U.S. Cl.
CPC ............ *C12M 23/16* (2013.01); *C12M 33/12* (2013.01); *C12M 41/46* (2013.01); *G01N 33/4836* (2013.01); *G01N 33/502* (2013.01)

(58) Field of Classification Search
CPC .. G01N 33/5005; G01N 33/502; C12M 23/16
See application file for complete search history.

(56) References Cited

U.S. PATENT DOCUMENTS

| RE43,122 E | 1/2012 | Harrison et al. |
| 2008/0233607 A1 | 9/2008 | Yu et al. |
| 2010/0003666 A1 | 1/2010 | Lee et al. |

(Continued)

OTHER PUBLICATIONS

Pearce et al., Integrated microelectrode array and microfluidics for temperature clamp of sensory neurons in culture. Lab Chip, vol. 5 (2005) pp. 97-101. (Year: 2005).*

(Continued)

*Primary Examiner* — Kara D Johnson
(74) *Attorney, Agent, or Firm* — Paula A. Borden; Rudy J. Ng; Bozicevic, Field & Francis LLP

(57) ABSTRACT

The present disclosure provides a microfluidics device for culturing cells, such as cardiomyocytes or cardiomyocyte progenitors; and methods of culturing cells using the device. The device and culturing methods find use in drug screening methods, for methods of evaluating a drug under development, and for methods of predicting patient response to a given treatment regimen, which methods are also provided.

28 Claims, 20 Drawing Sheets
Specification includes a Sequence Listing.

(56) References Cited

U.S. PATENT DOCUMENTS

| | | |
|---|---|---|
| 2010/0261222 A1 | 10/2010 | Sonntag et al. |
| 2011/0086427 A1 | 4/2011 | Faris et al. |
| 2012/0003732 A1 | 1/2012 | Hung et al. |
| 2012/0199487 A1 | 8/2012 | Stelzle et al. |

OTHER PUBLICATIONS

Zhao et al., Simultaneous orientation and cellular force measurements in adult cardiac myocytes using three-dimensional polymeric microstructures. Cell Motility and the Cytoskeleton, vol. 64 (2007) pp. 718-725. (Year: 2007).*

Ghibaudo, et al.; "Mechanics of cell spreading within 3D-micropatterned environments"; Lab on a Chip; vol. 11, No. 5, pp. 761-980 (Mar. 7, 2011).

* cited by examiner

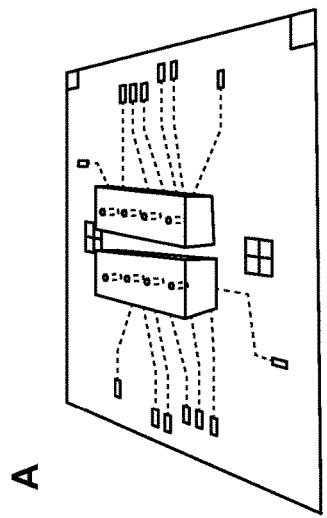
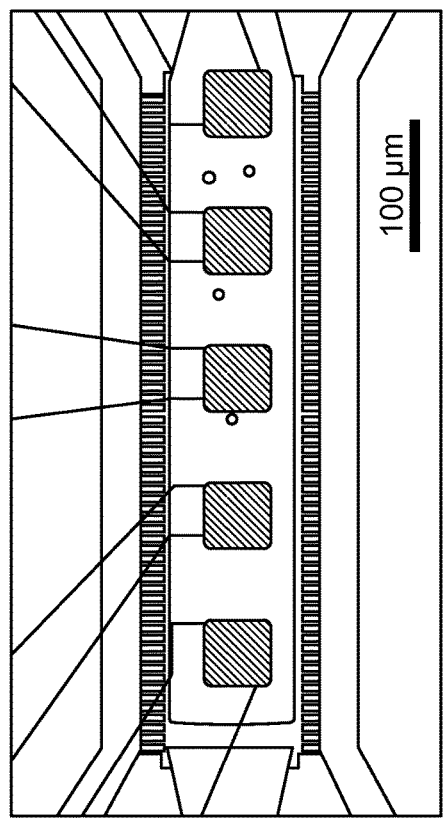
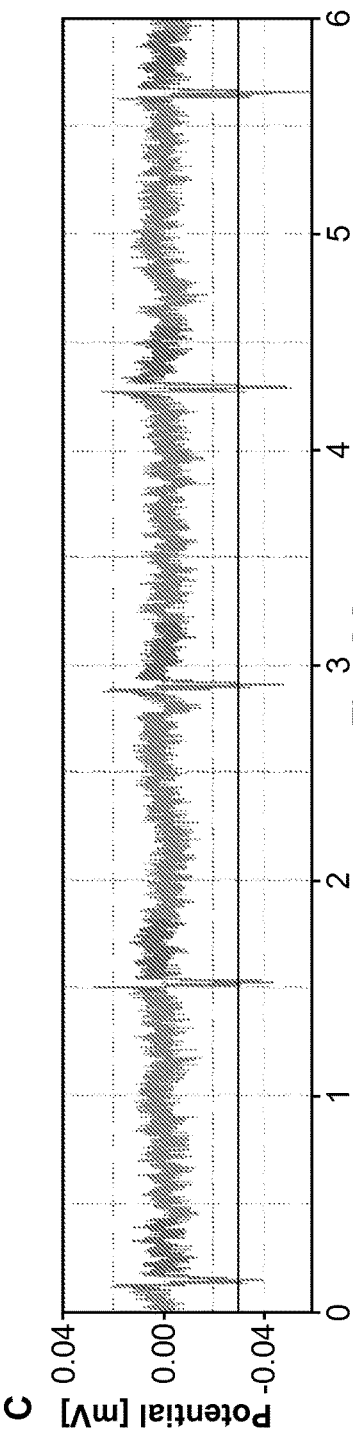
FIG. 5

| | Major parameters | Advantages |
|---|---|---|
| Motion Tracking | • Beat rate<br>• Contraction duration<br>• Contraction velocity | • Non-invasive<br>• Allows high throughput continuous monitoring<br>• Can be done in 3D or 2D culture<br>• Independent of underlying material<br>• No replating necessary |
| $Ca^{2+}$ reporter lines | • Beat rate<br>• Action potential duration<br>• $Ca^{2+}$ level | • Non-invasive<br>• Allows high throughput continuous monitoring<br>• Can be done in 3D or 2D culture<br>• Single cell-precision possible |
| MEA | • Beat rate<br>• Field potential duration<br>• Field potential amplitude | • Direct access of voltage |

FIG. 11

| Class | Drug | Pharmacology | Average ETPC$_{unbound}$[1] | Safety Margin = IC$_{50}$/ Average ETPC$_{unbound}$ |
|---|---|---|---|---|
| Ca$^{++}$ channel & hERG blocker | Verapamil | IC$_{50}$ = 950 nM | 45 nM | 21 |
| β stimulant | Isoproterenol | EC$_{50}$ = 315 nM | 1.75 nM | 180 |
| K$^+$ channel blocker | E-4031 | IC$_{50}$ = 392 nM | 1.9 nM | 206 |
| β β blocker | Metoprolol | IC$_{50}$ = 244 μM | 2.3 μM | 106 |
| Na$^+$ channel blocker | Flecainide | IC$_{50}$ = 6.7 μM | 0.7 μM | 9.6 |

FIG. 12

| Model | IC$_{50}$ (nM) | IC$_{50}$/Avg. ETPC$_{unbound}$ |
|---|---|---|
| 30 d EBs | 103.2 ± 6.03 | 2.3 |
| 82 d EBs | 410.65 ± 40.8 | 9.1 |
| 2D iPS | 169 ± 24 | 3.7 |
| Animal (pig heart) | 600 | 13.3 |
| MPS | 950 | 21.1 |

FIG. 13

MICROFLUIDICS CELL CULTURE DEVICE

CROSS-REFERENCE

This application claims the benefit of U.S. Provisional Patent Application No. 61/856,795, filed Jul. 22, 2013, which application is incorporated herein by reference in its entirety.

STATEMENT REGARDING FEDERALLY SPONSORED RESEARCH

This invention was made with Government support under Grant Number TR000487 awarded by the National Institutes of Health (NIH). The Government has certain rights in the invention.

INTRODUCTION

Drug discovery and development is hampered by high failure rates attributed to the reliance on non-human animal models employed during safety and efficacy testing. A fundamental problem in this inefficient process is that non-human animal models cannot adequately represent human biology and, more importantly, they cannot recapitulate human disease states. Ideally, the use of human disease specific tissues organized into a single integrated physiological system could have an enormous impact on the early screening of candidate drugs.

SUMMARY

The present disclosure provides microfluidic devices for culturing cells, such as cardiomyocytes or cardiomyocyte progenitors; and methods of culturing cells using the devices. The devices and culturing methods find use in drug screening methods, for methods of evaluating a drug under development, and for methods of predicting patient response to a given treatment regimen, which methods are also provided.

BRIEF DESCRIPTION OF THE DRAWINGS

FIGS. 5A-C depict a custom microelectrode array (MEA) for use with an MPS, according to an embodiment of the present disclosure.

FIG. 11 provides a table comparing different features of the real-time cardiac MPS functional measurements motifs, according to an embodiment of the present disclosure.

FIG. 12 provides a table with results from a cohort of drugs from different classes that have been tested in the cardiac MPS, according to an embodiment of the present disclosure.

FIG. 13 provides a table comparing verapamil's effect on different models and the MPS, according to an embodiment of the present disclosure.

DEFINITIONS

Figure 1:
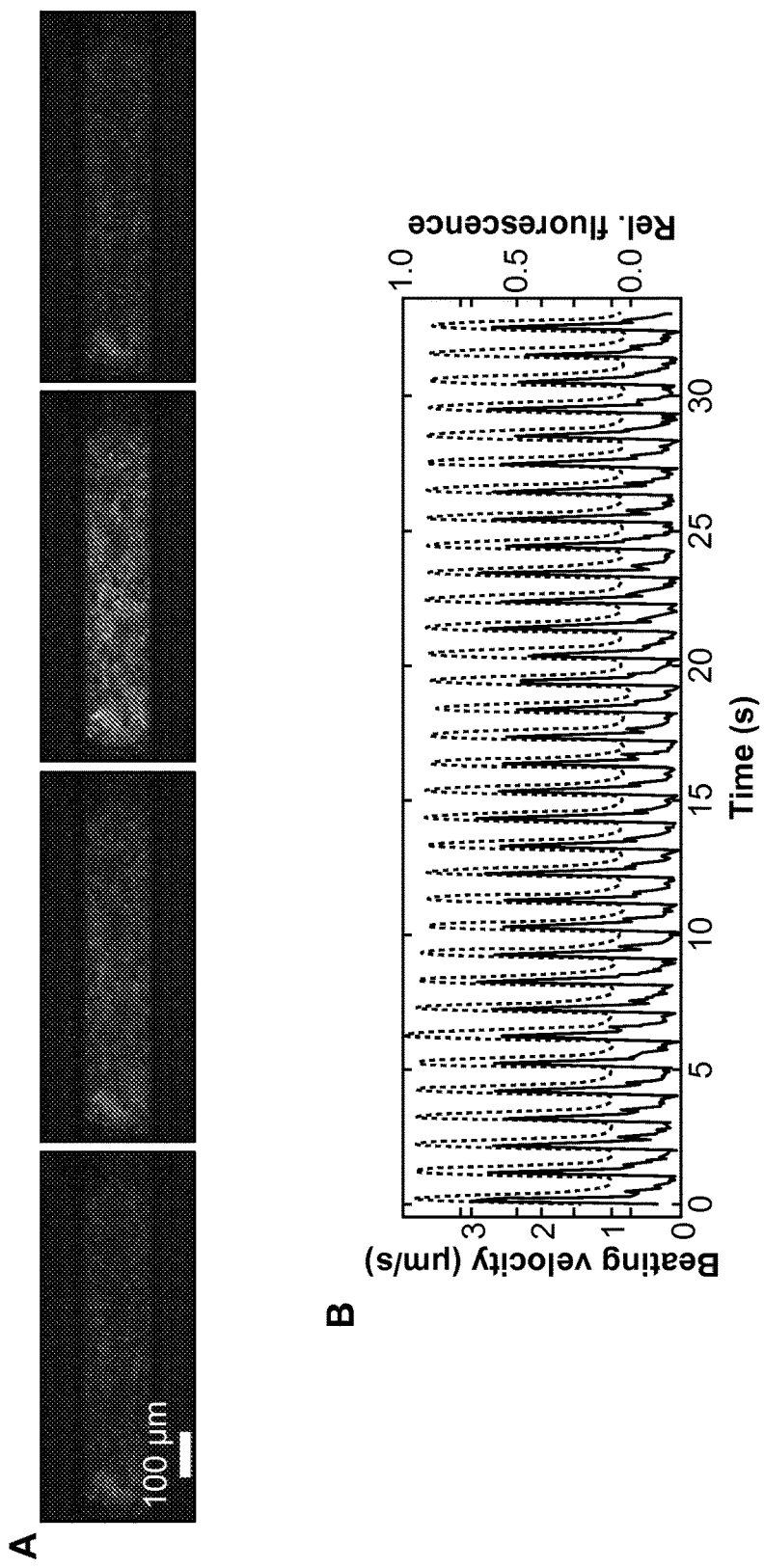
FIGS. 1A and 1B depict the use of a GCaMP6 $Ca^{2+}$ reporter construct in human induced pluripotent stem cell-derived cardiomyocytes (hiPSC-CMs), according to an embodiment of the present disclosure.

"Cardiovascular conditions or diseases" include, but are not limited to, coronary artery disease/ischemia, coronary artery disease (CAD), ischemia, angina (chest pain), thrombosis, coronary thrombosis, myocardial infarction (MI), silent ischemia, stenosis/restenosis, transient ischemic attack (TIA), atherosclerosis, peripheral vascular disease, bradyarrhythmia, e.g., bradyarrhythmia, bradycardia, sick sinus rhythm (Sick Sinus Syndrome), sinus bradycardia, sinoatrial block, asystole, sinus arrest, syncope, first degree atrioventricular (AV) block, second degree atrioventricular (AV) block, third degree atrioventricular (AV) block, chronotropic incompetence, tachyarrhythmia, e.g., tachyarrhythmia, tachycardia, fibrillation, flutter, atrial fibrillation, atrial flutter, familial atrial fibrillation, paroxysmal atrial fibrillation, permanent atrial fibrillation, persistent atrial fibrillation, supraventricular tachyarrhythmias, sinus tachycardia, reentry (reentrant arrhythmias), AV nodal reentry, focal arrhythmia, ectopy, ventricular fibrillation (VF), ventricular tachycardia (VT), Wolff-Parkinson-White Syndrome (WPW) and sudden cardiac death, heart failure, e.g., heart failure, cardiomyopathy, congestive heart failure, hypertrophic cardiomyopathy, remodeling, non-ischemic cardiomyopathy, dilated cardiomyopathy, restrictive cardiomyopathy, diastolic heart failure, systolic heart failure, and chronic heart failure, heart block/electrical disorders, e.g., atrioventricular (AV) block, bundle branch block (BBB), left bundle branch block (LBBB), right bundle branch block (RBBB), Long QT Syndrome (LQTS), premature ventricular contraction (PVC), electrical remodeling, intraventricular conduction defect, and hemiblock, hemodynamic deficiency, e.g., hypertension, hypotension, left ventricular dysfunction, low ejection fraction, low cardiac output, and low stroke volume, sudden cardiac death, cardiac arrest, sudden cardiac death (SCD), ventricular fibrillation, and pump failure, as well as bacterial endocarditis, viral myocarditis, pericarditis, rheumatic heart disease, and syncope. In particular, a cardiovascular condition includes, but is not limited to, arrhythmia, e.g., atrial fibrillation, ventricular fibrillation or bradycardia, ischemia, heart failure and hyperplasia not associated with neoplastic disease, which condition may be associated with ventricular remodeling, diastolic dysfunction, aberrant body temperature, aberrant or altered pressure, e.g., altered venous, left ventricular or left atrial pressure, aberrant or altered heart rate or sounds, aberrant or altered electrogram, aberrant or altered cardiac metabolism, such as altered blood pH, glucose, $pO_2$, $pCO_2$, minute ventilation, creatine, CRP, Mef2A, creatine kinase or creatine kinase MB levels, aberrant or altered pulmonary or thoracic impedance, aberrant or altered stroke volume, aberrant or altered neurohormone levels, aberrant or altered electrical activity, aberrant or altered sympathetic nerve activity, aberrant or altered renal output, aberrant or altered filtration rate, aberrant or altered angiotensin II levels, or aberrant or altered respiratory sounds, and the like.

The term "induced pluripotent stem cell" (or "iPS cell"), as used herein, refers to a stem cell induced from a somatic cell, e.g., a differentiated somatic cell, and that has a higher potency than said somatic cell. iPS cells are capable of self-renewal and differentiation into mature cells, e.g. cells of mesodermal lineage or cardiomyocytes. iPS may also be capable of differentiation into cardiac progenitor cells.

As used herein, the term "stem cell" refers to an undifferentiated cell that can be induced to proliferate. The stem cell is capable of self-maintenance, meaning that with each cell division, one daughter cell will also be a stem cell. Stem cells can be obtained from embryonic, fetal, post-natal, juvenile or adult tissue. The term "progenitor cell", as used herein, refers to an undifferentiated cell derived from a stem cell, and is not itself a stem cell. Some progenitor cells can produce progeny that are capable or differentiating into more than one cell type.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some embodiments, the individual is a human. In some embodiments, the individual is a murine.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cardiomyocyte" includes a plurality of such cardiomyocytes and reference to "the microfluidics device" includes reference to one or more microfluidics devices and equivalents thereof known to those skilled in the art, and so forth. It is further noted that the claims may be arartea to excivae any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides microfluidic devices for culturing cells, such as cardiomyocytes or cardiomyocyte progenitors; and methods of culturing cells using the devices. The devices and culturing methods find use in drug screening methods, for methods of evaluating a drug under development, and for methods of predicting patient response to a given treatment regimen, which methods are also provided.

Microfluidic Devices

Aspects of the disclosure include microfluidic devices that are adapted for receiving and culturing a plurality of cells. Microfluidic devices in accordance with embodiments of the invention are three-dimensional structures that are configured to provide an environment that is suitable for culturing cells. The subject microfluidic devices are also configured to deliver a cell culture medium to the cells that are cultured within the device.

Microfluidic devices in accordance with embodiments of the invention include a cell culture channel. The cell culture channel may have any of a variety of geometries and dimensions that are suitable for receiving and culturing cells therein. The cell culture channel is a three-dimensional structure that includes a base and two walls that extend from a first end to a second end of the channel. The first end of the cell culture channel is referred to as the "inlet end" and the second end of the cell culture channel is referred to as the "outlet end." The distance from the inlet end to the outlet end defines the length of the cell culture channel. In some embodiments, the length of the cell culture channel ranges from 0.6 mm to 5 mm, such as 0.8, 1, 1.5, 2, 2.5, 3, 3.5, 4, or 4.5 mm; e.g., the length of the cell culture channel can range from 0.6 mm to about 1 mm, from about 1 mm to about 2 mm, from about 2 mm to about 3 mm, from about 3 mm to about 4 mm, or from about 4 mm to about 5 mm. The distance between the two walls in the direction that is perpendicular to the length of the channel defines the width of the channel. In some embodiments, the width of the cell culture channel ranges from 30 µm to 200 µm, such as 40, 50, 60, 70, 80, 90, 100, 110, 120, 130, 140, 150, 160, 170, 180 or 190 µm; e.g., the width of the cell culture channel can range from about 30 µm to about 50 µm, from about 50 µm to about 75 µm, from about 75 µm to about 100 µm, from about 100 µm to about 125 µm, from about 125 µm to about 150 µm, from about 150 µm to about 175 µm, or from about 175 µm to about 200 µm. The distance from the base of the channel to the top of the walls defines the height of the cell culture channel. In some embodiments, the height of the channel ranges from 30 to 200 µm, such as 40, 50, 60, 70, 80, 90, 100, 110, 120, 130, 140, 150, 160, 170, 180 or 190 µm; e.g., the height of the cell culture channel can range from about 30 µm to about 50 µm, from about 50 µm to about 75 µm, from about 75 µm to about 100 µm, from about 100 µm to about 125 µm, from about 125 µm to about 150 µm, from about 150 µm to about 175 µm, or from about 175 µm to about 200 µm.

Microfluidic devices in accordance with embodiments of the invention include two media channels that are disposed on either side of the cell culture channel and are configured to contain and transport a fluid medium. The media channels are three-dimensional structures and may have any of a variety or geometries and dimensions that are suitable for transporting a fluid medium. Each of the media channels includes a segment or portion that is disposed in close proximity to the cell culture channel and extends along the length of the cell culture channel.

Each media channel includes a base and two walls that extend from a first end of the channel to a second end of the channel. The distance from the first end of the media channel to the second end of the media channel defines the length of the media channel. In some embodiments, the length of each media channel is greater than or equal to the length of the cell culture channel. The distance between the two walls of the media channel in the direction that is perpendicular to the length of the channel defines the width of the channel. In some embodiments, the width of the media channel ranges from 20 µm to 100 µm, such as 30, 40, 50, 60, 70, 80 or 90 µm. The distance from the base of the media channel to the top of the walls defines the height of the media channel. In some embodiments, the height of the media channel ranges from 30 µm to 200 µm, such as 40, 50, 60, 70, 80, 90, 100, 110, 120, 130, 140, 150, 160, 170, 180 or 190 µm.

Each media channel is fluidly connected to the cell culture channel via a plurality of microchannels that are adapted to prevent cells from migrating between the cell culture channel and the media channels. As such, the microchannels have dimensions that allow fluid (e.g., cell culture medium) to pass through, but prevent the passage of cells. Each microchannel includes a base and two walls. In some embodiments, the height of each microchannel ranges from 0.1 µm to 5 µm, such as 0.5, 1, 1.5, 2, 2.5, 3, 3.5, 4, or 4.5 µm. In some embodiments, the width of each microchannel ranges from 0.1 µm to 5 µm, such as 0.5, 1, 1.5, 2, 2.5, 3, 3.5, 4, or 4.5 µm. The length of each microchannel is defined by the distance between the inner surface of the wall of the cell culture channel and the inner surface of the adjacent wall of the media channel. In some embodiments, the length of each microchannel ranges from 8 µm to 20 µm, such as 10, 12, 14, 16, or 18 µm. In certain embodiments, the length of each microchannel is 10 µm.

As used herein, the term "pitch" means the distance between two adjacent structures (e.g., two adjacent microchannels), as measured from the center of the first structure to the center of the second, adjacent structure. In some embodiments, the pitch of the microchannels ranges from 2 µm to 20 µm, such as 4, 6, 8, 10, 12, 14, 16, or 18 µm.

In some embodiments, the cell culture channel includes one or more alignment components that are adapted to align the cell culture channel and the media channels with the microchannels to ensure proper fluid communication between the cell culture channel and media channels. In some embodiments, the alignment component is disposed on a wall of the cell culture channel and has a height ranging from 0.1 µm to 5 µm, such as 0.5, 1, 1.5, 2, 2.5, 3, 3.5, 4, or 4.5 µm. In some embodiments, the alignment component has a thickness ranging from 1 to 5 µm, such as 1.5, 2, 2.5, 3, 3.5, 4 or 4.5 µm.

In some embodiments, the cell culture channel includes a weir that is disposed near the outlet of the channel and is configured to trap cells within the cell culture channel while allowing fluid to pass. As such, the weir is configured or adapted to partially block the outlet of the cell culture channel. The width of the weir is equal to the width of the cell culture channel, such that the weir extends across the entire width of the cell culture channel. The height of the weir is less than the height of the cell culture channel, such that in use, fluid is able to pass through a gap, or space between the bottom of the weir and the base of the cell culture channel, while cells are retained within the cell culture channel. In some embodiments, the difference between the height of the weir and the height of the cell culture channel ranges from 1 µm to 5 µm, such as 1.5, 2, 2.5, 3, 3.5, 4 or 4.5 µm. In use, the weir provides for low pressure loading of cells into the cell culture channel because fluid can pass through the gap between the weir and the base of the cell culture channel, while cells are retained within the channel. Fluid can pass through the gap under the weir and out through the outlet of the cell culture channel without having to pass through the microchannels. This configuration facilitates loading cells into the cell culture channel at low pressure (e.g., a pressure ranging from 25 Pa to 75 Pa, such as 30, 35, 40, 45, 50, 55, 60, 65, or 70 Pa) by avoiding the increase of pressure associated with forcing fluid through the microchannels. In some embodiments, cells are loaded into the cell culture channel at a pressure of 50 Pa using gravitational loading with a liquid height ranging from 0.2 cm to 0.8 cm, such as 0.5 cm.

In some embodiments, the cell culture channel includes one or more sensors that are adapted to collect data from cells that are cultured within the microfluidic device. In some embodiments, the number of sensors ranges from 1 to 50, such as 2, 3, 4, 5, 6, 7, 8, 9, 10, 12, 15, 20, 25, 30, 35, 40, or 45 sensors. The sensors are generally disposed on a surface of the cell culture channel, such as on the base or the cell culture channel, and are adapted to contact a plurality of cells that are cultured in the device. The sensors may be located at various positions within the device, such as, e.g., disposed on the base of the cell culture channel, on a wall of the cell culture channel, at or near the inlet or the outlet of the cell culture channel, etc. In some embodiments, one or more sensors are disposed on an interior surface of a flat substrate that seals the device, as described further herein.

In some embodiments, a sensor is a mechanosensing pillar that is configured to collect data that relates to the mechanical activity of the cells that are cultured in the device. For example, in certain embodiments, a mechanosensing pillar is configured to measure a force created by a contraction of one or more cells that are cultured in the device. In some embodiments, a mechanosensing pillar may be configured to measure other types of data from the cells that are cultured in the device, such as the frequency at which certain forces are generated by contraction of the cells.

A mechanosensing pillar in accordance with embodiments of the invention has a height that is measured from the base of the cell culture channel to the top of the pillar. In some embodiments, the height of the mechanosensing pillar is 1 μm to 5 μm less than the height of the cell culture channel, such as 1.5, 2, 2.5, 3, 3.5, 4 or 4.5 μm less than the height of the cell culture channel. The cross-sectional shape of the mechanosensing pillar can be circular, square, rectangular, hexagonal, or any other suitable shape. The length and width of the mechanosensing pillar can each range from 5 to 25 μm, such as 10, 15 or 20 μm. In some embodiments, a mechanosensing pillar has a spring constant that describes the force necessary to displace, deflect, bend or move the sensor by a given distance. In certain embodiments, the spring constant of a mechanosensing pillar ranges from 0.005 μN/μm to 1 μN/μm, such as 0.01, 0.05, 0.1, or 0.5 μN/μm. Mechanosensing pillars in accordance with embodiments of the invention can be made from any suitable material, including but not limited to elastomeric materials, such as polydimethylsiloxane (PDMS).

In some embodiments, a sensor is an electrode that is configured to collect data that relates to the electrical activity of the cells that are cultured in the device. For example, in certain embodiments, an electrode is configured to measure a voltage potential, a field potential, or a current that is generated by one or more cells that are cultured in the device. In some embodiments, an electrode may be configured to measure the amplitude and/or frequency of the electrical activity of the cells.

In some embodiments, a sensor includes a multi-electrode array (MEA) chip that comprises a plurality of individual electrodes. An MEA chip may include different types of electrodes, including, e.g., measurement electrodes and reference electrodes. In some embodiments, an MEA chip includes 2 to 10 measurement electrodes, such as 3, 4, 5, 6, 7, 8 or 9 measurement electrodes. In some embodiments, an MEA chip includes 1 or 2 reference electrodes. In some embodiments, an MEA chip is irreversibly bonded to the device.

In some embodiments, a measurement electrode is disposed on a bottom surface of the cell culture channel, i.e., on the base of the cell culture channel. In some embodiments, a measurement electrode is disposed on a wall of the cell culture channel. In some embodiments, a reference electrode is disposed on a bottom surface of the cell culture channel, i.e., on the base of the cell culture channel. In some embodiments, a reference electrode is disposed on a wall of the cell culture channel. In certain embodiments, a reference electrode is disposed in the outlet of the cell culture channel and/or in the inlet of the cell culture channel. In some embodiments, one or more electrodes are disposed on an interior surface of a flat substrate that seals the device, as described further herein.

Electrodes in accordance with embodiments of the invention can be made from any suitable material, including but not limited to indium tin oxide, gold, platinum black, or platinum, and may have any suitable geometry and/or dimensions. In some embodiments, an electrode has a rectangular shape and has an edge length that ranges from 20 μm to 300 μm, such as 40, 60, 80, 100, 120, 140, 160, 180, 200, 220, 240, 260 or 280 μm. In some embodiments, an electrode has a circular shape and has a diameter that ranges from 20 μm to 300 μm, such as 40, 60, 80, 100, 120, 140, 160, 180, 200, 220, 240, 260 or 280 μm. In certain embodiments, a measurement electrode has a rectangular shape and has an edge length that ranges from 20 μm to 50 μm, such as 30 or 40 μm. In certain embodiments, a measurement electrode has a circular shape and has a diameter that ranges from 20 μm to 50 μm, such as 30 μm or 40 μm. In certain embodiments, a reference electrode has a rectangular shape and has an edge length that ranges from 50 μm to 300 μm, such as 60, 80, 100, 120, 140, 160, 180, 200, 220, 240, 260 or 280 μm. In certain embodiments, a reference electrode has a circular shape and has a diameter that ranges from 50 μm to 300 μm, such as 60, 80, 100, 120, 140, 160, 180, 200, 220, 240, 260 or 280 μm.

Microfluidic devices in accordance with embodiments of the invention may have a plurality of ports that are configured to allow the introduction and/or removal of fluid from the device. For example, in some embodiments, a device includes one or more ports that are configured to allow the introduction of cell culture medium into the media channels of the device. In some embodiments, a device includes a port that is configured to allow the introduction of a fluid that comprises cells into the cell culture channel of the device. The ports are configured such that fluid connections can readily be established under sterile conditions, as desired, to add and/or remove one or more fluids from the device. In some embodiments, a device may include a number of ports ranging from 1 to 10, such as 2, 3, 4, 5, 6, 7, 8 or 9 ports.

Microfluidic devices in accordance with embodiments of the invention can be made from any of a variety of suitable materials, including but not limited to elastomers (e.g., polydimethylsiloxane (PDMS)), thermosets (e.g., polyimide, polyurethane, SU-8), thermoplastics (e.g., polymethylmethacrylate (PMMA), polycarbonate (PC), polystyrene (PS), polyethylene terephthalate (PET) or polyvinylchloride (PVC)), or other materials, such as glass, quartz, or silicon. Combinations of two or more of the aforementioned materials can also be used.

In some embodiments, fabrication of the subject devices is accomplished using multilayer photolithography and molding techniques. In some embodiments, a rigid mold is created using multilayer photolithography, and then the mold is used to cast the device in a suitable material, e.g., and elastomeric material, such as PDMS.

In some embodiments, a polyepoxide (epoxy) resin is used as a photoresist material in the mold fabrication process. In the mold fabrication process, a silicon wafer is cleaned with a mixture of 70% sulfuric acid and 30% hydrogen peroxide by volume, followed by a dehydration bake. The wafer is then spin-coated with a layer of photoresist material (e.g., SU8-2001 (MicroChem Corp, MA, USA)) and subsequently soft-baked to evaporate residual solvents from the photoresist film. Then, the substrate is patterned via conventional UV photolithography. A chrome photomask with desired device features (e.g., the microchannels that connect the media channels and the cell culture channel) is formed for the first level of lithography. The photoresist is then exposed to UV light on a mask aligner (Karl Suss MA-6). After exposure, the wafer is postbaked on a hot plate and developed with a developer (SU-8 developer, MicroChem Corp, MA, USA). Next, the wafer is hard baked.

In some embodiments, the fabrication process includes a second level of photolithography to create additional features of the device. For the second level of photolithography, the wafer is coated with another layer of photoresist and soft-baked on a hot plate. A second chrome photomask with desired device features is formed for the second level of photolithography. The photoresist is exposed to UV light on a mask aligner and post-exposure baked and/or developed with a developer as needed to create a photoresist mold that can be used to cast a microfluidic device. In some embodiments, multiple levels of photolithography are used to create the mold, such as 2, 3, or 4 levels of photolithography. In some embodiments, a positive or a negative photoresist material may be utilized in any level of the photolithography process, as needed, to create a desired feature of the microfluidic device mold.

Following production of the microfluidic device mold, the microfluidic device is cast in an elastomeric material. In some embodiments, the photoresist mold is contacted with a material that facilitates the release of the elastomeric material from the mold following the casting process. Examples of materials that facilitate the release of the elastomeric material from the mold include, but are not limited to, trichlorosilane (Gelest, Inc). To cast the device in the mold, the elastomeric material, e.g., PDMS (Sylgard 184, Dow Corning) is mixed thoroughly with a curing agent in a suitable ratio (e.g., a ratio of 10:1) and degassed in a vacuum chamber to remove any trapped air. The mixture is then poured into the mold and cured at a designated temperature for a sufficient amount of time for the elastomeric material to cure. In some embodiments, the curing process is conducted at a temperature of 65° C. for a period of 12 hours. The elastomeric material is then removed from the mold.

Additional features of the microfluidic device can be added after the molding process has been completed. For example, in some embodiments, fluidic ports may be added to the device by removing a portion of the device material using a suitable instrument, such as, e.g., a 1 mm biopsy punch (Harris Uni-Core).

Following molding and curing, the microfluidic device is bonded to a flat substrate to seal the device. In some embodiments, the flat substrate comprises a glass coverslip. In some embodiments, the bonding process is facilitated by oxidizing the device and the substrate (e.g., a glass coverslip) in a suitable environment, such as an oxygen plasma environment, under suitable conditions. In some embodiments, oxidizing is conducted in an oxygen plasma environment for 20 seconds at 60 W, 10 atm $cm^3$/min, and 20 mTorr.

In some embodiments, one or more surfaces of the device are contacted with a compound that is adapted to promote adhesion of cells to the device. Examples of compounds that promote adhesion of cells to the device include but are not limited to fibronectin (Invitrogen). In some embodiments, the compound that promotes adhesion of cells to the device is placed in solution (e.g., in phosphate buffered saline (PBS)) and is incubated with the device under suitable conditions for the compound to sufficiently adhere to the surface of the device. In some embodiments, the compound that promotes adhesion of cells to the device is deposited in a desired pattern on a surface of the device in order to promote adhesion of cells in the desired pattern.

Aspects of the disclosure include systems that find use in conjunction with the microfluidic devices described herein. In some embodiments, a system includes a computational motion capturing component that is configured to image a plurality of cells that are cultured within a subject microfluidic device. In some embodiments, the computational motion capturing component is configured to detect a magnitude, velocity and/or direction of a motion made by a cell (e.g., a contraction of a cardiomyocyte) with high spatial and temporal resolution. In some embodiments, the computational motion capturing component includes a camera that can capture images of cells that are cultured within the device, and includes an algorithm that is adapted to determine a motion vector for a defined area of a captured image over a specified time interval. In some embodiments, the algorithm can be used to determine a motion vector for a defined area of cells, or for an individual cell. Using the subject computational motion capturing component, the spatial distribution of the time-averaged movement velocity of a plurality of cells can be measured. In some embodiments, the computational motion capturing component can be used to determine absolute movement, as well as movement in a single coordinate direction, e.g., in the x-direction and/or in the y-direction. In some embodiments, the computational motion capturing component can be used to determine movement data as a function of time, as well as movement in a single coordinate direction, e.g., in the x-direction and/or in the y-direction, as a function of time. In some embodiments, the computational motion capturing system can be used to measure parameters such as mean contraction velocity, contraction angle, or mean contraction velocity in the x-direction and/or y-direction.

In some embodiments, the computational motion capturing component is configured to measure the displacement of one or more mechanosensing pillars in the device. The displacement of a mechanosensing pillar in the x- and/or y-direction can be used to determine the forces that are exerted on the mechanosensing pillar by the cells that are cultured in the device, and can thus be used to conduct a mechanocardiogram analysis to determine, e.g., a beat rhythm for a plurality of cardiomyocytes that are cultured in the device. Image capture software is used to determine the position of a mechanosensing pillar as a function of time. The deflection or displacement of the mechanosensing pillar is then determined by comparing the relative positions of the pixels in a plurality of images of the mechanosensing pillar that are captured over a specified time period (e.g., a specified acquisition rate). In some embodiments, a plurality of images is collected at a rate of 10 frames per second for a total of 30 seconds.

Additional aspects of the disclosure include peripheral components that can be used in conjunction with the subject devices. For example, in some embodiments, the subject systems include pumps, valves, mass flow controllers, reservoirs, sterile filters, syringes, pipettes, and/or any other fluid handling devices or components. In some embodiments, the subject systems include microscopy equipment that can be used to image the device and the cells that are cultured within the device at a suitable magnification to facilitate observation of the cells and collection of data from the cells.

Figure 2:
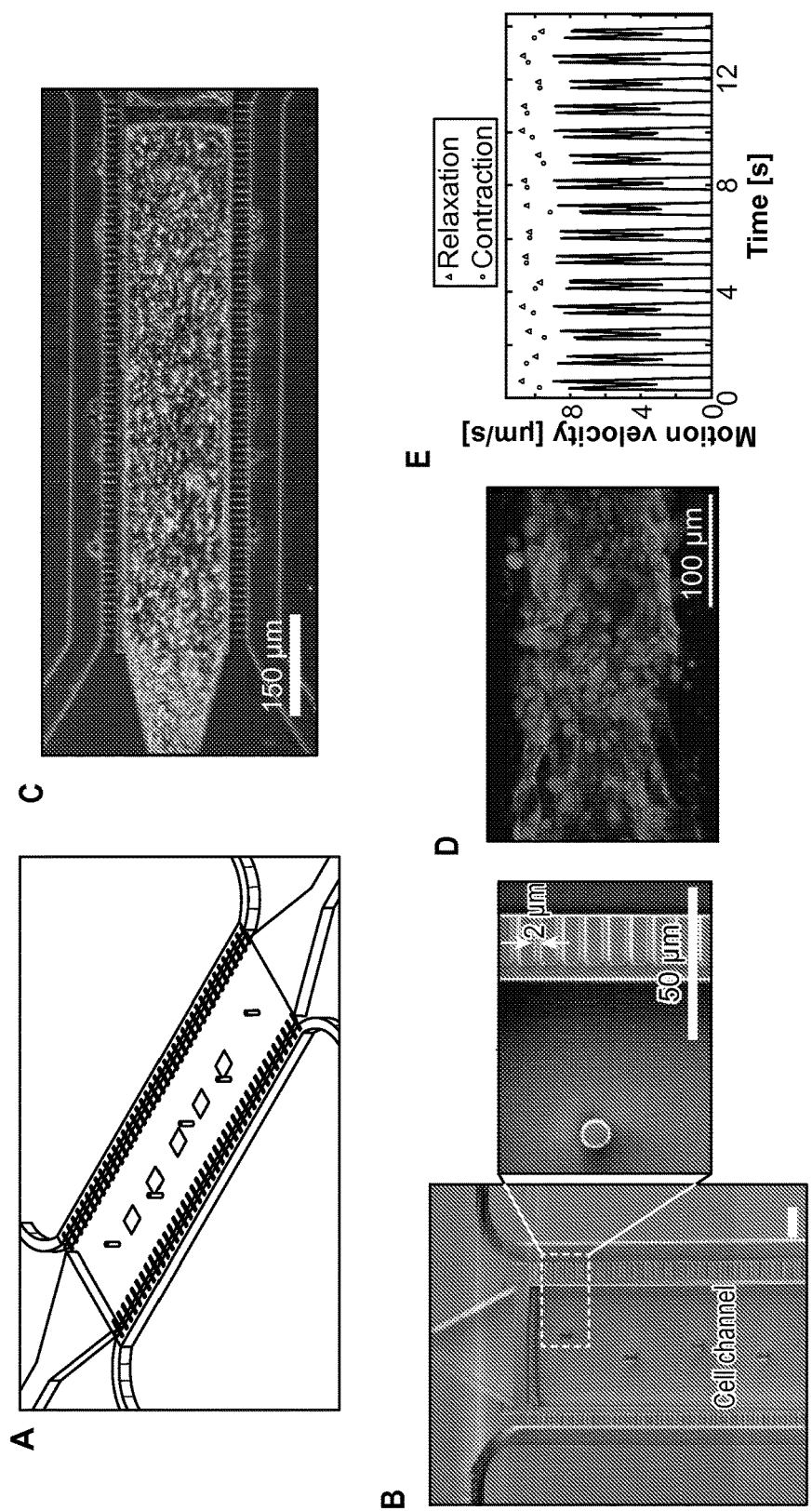
FIGS. 2A-E depict a cardiac microphysiological system (MPS) microfluidic device and its use, according to an embodiment of the present disclosure.

Referring now to FIG. 2, an embodiment of a microfluidic device is shown. As depicted in FIG. 2, panel A, the device includes a cell culture channel and two media channels that are connected via a plurality of microchannels. The depicted cell culture channel includes a plurality of electrodes and mechanosensing pillars. Panel B shows a magnified scanning electron microscope image of a microfluidic device, and in the inset provides an additional magnification of a mechanosensing pillar and a plurality of microchannels that fluidly connect the cell culture channel to a media channel. Panel C shows in image of a microfluidic device that contains a plurality of cells within the cell culture channel. The weir, positioned at the outlet of the cell culture channel, serves to retain the cells within the cell culture channel during the loading process as well as during culture.

Referring now to FIG. 5, an embodiment of a microfluidic device that has been bonded to a multi-electrode array (MEA) is shown. Panel A shows various conductive leads that feed into the MEA. Panel depicts a microfluidic device with five electrodes located in the cell culture channel. The depicted device also includes a plurality of mechanosensing pillars, as well as a weir located at the outlet of the cell culture channel.

Figure 17:
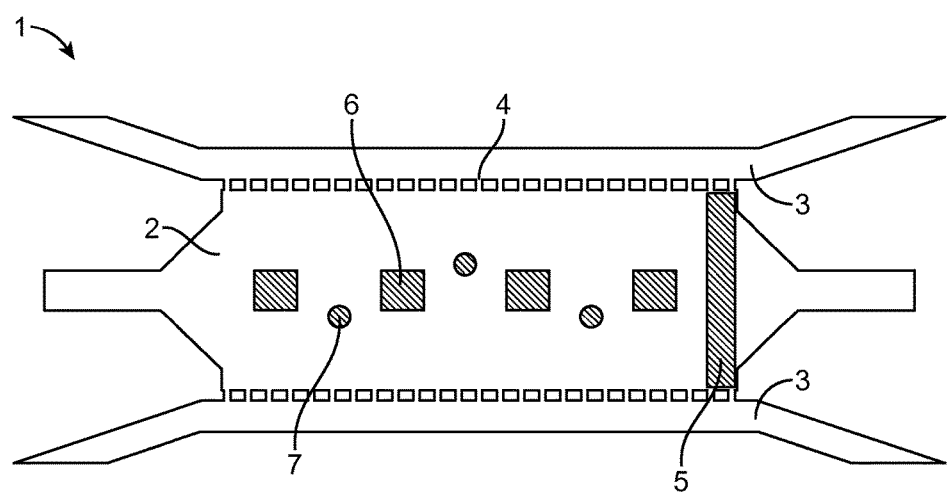
FIG. 17 depicts an overhead view of an embodiment of a subject microfluidic device.

Referring now to FIG. 17, an overhead view of an embodiment of a microfluidic device 1 is shown. The depicted microfluidic device 1 includes a cell culture channel 2 and two media channels 3. The cell culture channel 2 is fluidly connected to both of the media channels 3 via a plurality of microchannels 4. The cell culture channel 2 in the depicted embodiment also includes a weir 5. Within the depicted cell culture channel 2 are a plurality of sensors (6, 7). The depicted sensors include electrodes 6 as well as mechanosensing pillars 7.

Figure 18:
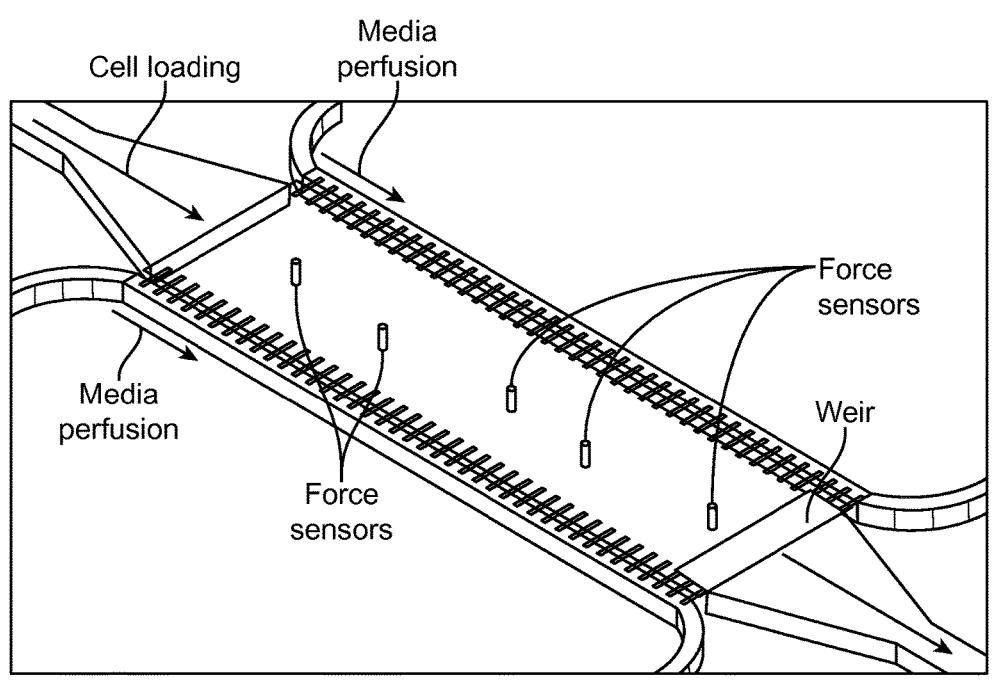
FIG. 18 depicts a three-dimensional schematic representation of a subject microfluidic device.

Referring now to FIG. 18, a three-dimensional schematic representation of a subject microfluidic device is shown. The depicted device includes a cell culture channel with an inlet for cell loading and an outlet. The cell culture channel also includes a weir. There are two media channels, one disposed on either side of the cell culture channel. The media channels are connected to the cell culture channel via a plurality of microchannels. The direction of media perfusion is depicted with an arrow along each media channel. In the depicted embodiment, media perfusion proceeds in the direction from the inlet end of the cell culture channel, towards the outlet end of the cell culture channel, where the weir is located. The depicted embodiment also includes a plurality of mechanosensing pillars that are adapted to measure forces exerted by cells in the cell culture channel when the device is in use.

Figure 19:
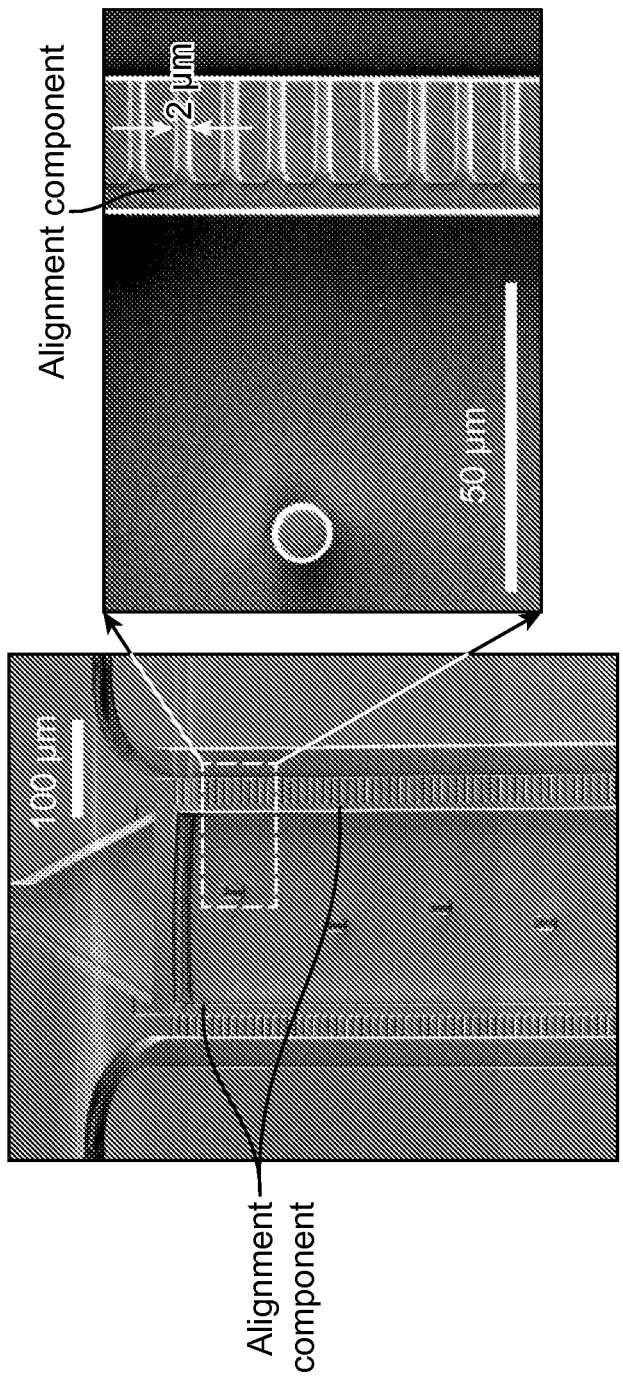
FIG. 19 depicts a scanning electron microscope image of a subject microfluidic device.

Referring now to FIG. 19, a scanning electron microscope image of a subject microfluidic device is shown. The image shows an outlet end of a cell culture channel, where a weir is located. The image also shows two media channels disposed on either side of the cell culture channel. The media channels are fluidly connected to the cell culture channel via a plurality of microchannels. Also depicted are a plurality of mechanosensing pillars that are adapted to measure forces exerted by the cells in the cell culture channel when the device is in use. The image also shows an alignment component that is adapted to align the cell culture channel and the media channels to ensure fluid communication via the microchannels. In the further-magnified segment of the image, the alignment component is shown adjacent the microchannels. A mechanosensing pillar is also shown in the further-magnified segment of the image.

Figure 20:
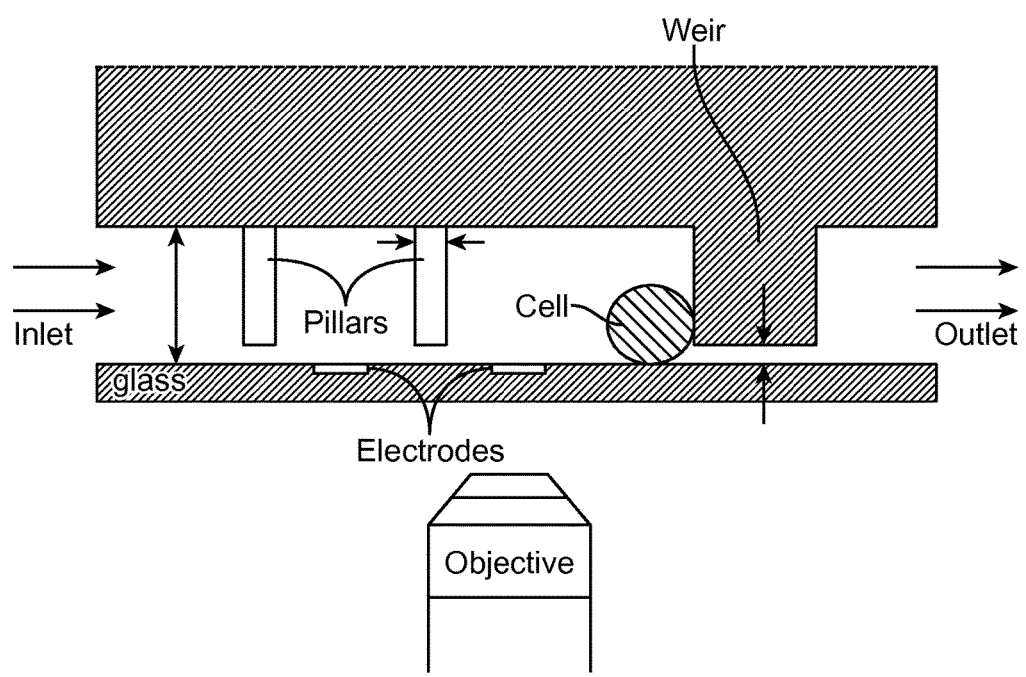
FIG. 20 depicts a profile view illustration of a subject microfluidic device with a representation of a cell retained therein.

Referring now to FIG. 20, a profile view of a subject microfluidic device is illustrated. In the illustration, a glass substrate is fixed over the device to seal the device, and the device has been inverted so that the depicted mechanosensing pillars and the weir extend downward. A microscope objective is depicted underneath the device for visualizing cells within the device by viewing the device from below. The inlet end of the cell culture channel is depicted on the left-hand side, and the outlet end of the cell culture channel is depicted on the right-hand side, near the weir. The gap, or space, between the weir and the glass substrate can be seen. In the depicted device, two electrodes are disposed on the glass substrate.

Also depicted in the illustration is a cell that has been placed within the device. The depicted cell is inside the device and sits in the cell culture channel. As can be seen, the cell is retained in the cell culture channel by the weir. The depicted cell is too large to pass through the gap between the weir and the glass substrate.

Example of a Biomimetic Microfluidic 3D Culture System

In some cases, a microfluidic three-dimensional (3D) culture system of the present disclosure is capable of providing an environment for cell culturing and differentiation, and comprises three open ended channels with a large fluidic flow cross-section, which are interconnected by an array of microchannels (dimensions; 0.1 µm-5 µm width and height, 10 µm length and 2 µm-20 µm pitch). The central channel is designated as the cell culture channel (dimensions; 30 µm-200 µm width and height and 0.6 mm-5 mm length) with a large fluidic flow inlet cross-section allowing the loading of cells; the two adjacent outer channels are designated as media channels (dimensions: 20 µm-100 µm width and 30 µm-200 µm height). These channels facilitate adequate flow conditions for culture medium and/or reagents. The interconnecting microchannels provide sufficient fluidic connection to allow media or reagents to diffuse through while preventing cell migration to the media channel. To make sure that the cell channel and media channel are aligned with the microchannels, the sides of the culture channel feature an overhang of 0.1 µm-5 µm height and a depth of 1 µm-5 µm. Four ports serve as inlet and outlets for cell loading and media flow.

The three functional components of the microfluidic device mimic the physiological environment in the human body. The cell culture channel mimics the space between perimysial collagen fibers in the myocardium of the human heart and organizes the alignment of CMs into a beating microtissue, The media channel for nutrient transport mimic the capillaries, which have a lumen diameter of ~5 µm-15 µm, The microchannels act as artificial endothelial barriers allowing diffusive transport of nutrients from the media channel to the cell channel.

The device is capable of culturing hiPSCs, cardiac and other tissues over multiple weeks. It can also be used as a controlled environment to differentiate stem cells into different lineages. Functionality of the device has been verified using hiPS cells differentiated into cardiac myocytes (hiPSC-CMs), which when seeded show consistent beat rate over multiple weeks in medium with and without serum.

Open-Ended Design with a Weir at End for Increased Cell Trapping:

In exemplary embodiments, the outlet of the cell channel is partially blocked by a weir. This weir is attached to the ceiling and has a clearance of 1 µm-5 µm to the floor. This design of the tissue channel allows for a fast and dense loading of cells, while still enabling an unloading of the cells post screening. Thereby, ex situ analysis tools (e.g. flow cytometry, qPCR) can be employed.

Hybrid System Capable of Mechanical, Electrical, and Computational Measurements:

To compute the forces exerted by beating CMs, the cell culture channel is equipped with 2-10 cylindrical and/or rectangular shaped mechanosensing pillars (spring constants 0.005 µN/pm-1 µN/pm) distributed throughout the cell channel. There is a clearance of 1-5 µm between the lower end of the pillars and the floor—Inclusion of the pillars within a 3d microtissue gives the forces exerted by the tissue, this can be calculated by assuming a distributed load along the length of the pillar.

Real-time field potential measurements can be done using an in-house multi electrode array (MEA) chip. The MEA chip can be irreversibly bonded to the device such that 2-10 micro electrodes are distributed in the floor of the culture channel and 1-2 reference electrodes are located in the floor of the in- and/or outlet of the culture channel. The micro electrodes, made of indium tin oxide, gold, platinum black, or platinum, are rectangular or circular shaped with an edge length/diameter of 20 µm-50 µm and the reference electrodes are rectangular or circular shaped with an edge length/diameter of 50 µm-300 µm.

A computational motion capturing method additionally enables the offline analysis of the beating tissue. A motion capture software detects the magnitude, velocity, and direction of the contraction with a high spatial and temporal resolution. Using block matching algorithms, the motion vector of the macroblocks of definable size are determined for each timestep.

The temporal and spatial resolution is thereby only limited by the camera specification, the frame rate and the image resolution respectively.

Figure 14:
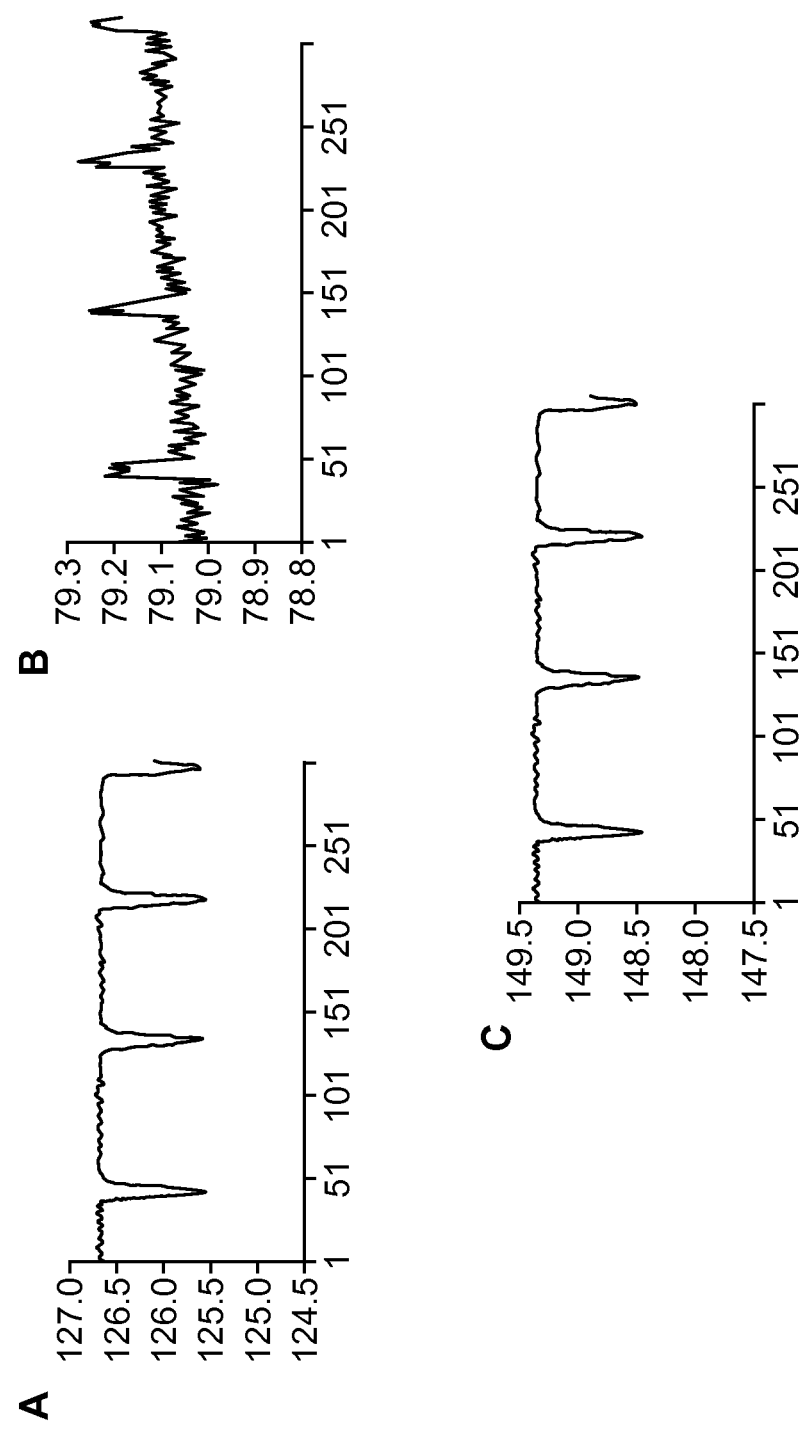
FIGS. 14A-C depict deflection of the pillar to measure the beat rate or cardiac tissue in an exemplary device.

The Mechanocardiogram (MCG) is a noninvasive procedure for recording the beat rate and the rhythm of the heart. It is an alternative method for diagnosing various cardiac abnormalities, for example, ischemic heart disease, arrhythmias (irregular heart beat), tachycardia (fast heartbeat), bradycardia (slow heartbeat), myocardial infarction (heart attack), and certain congenital heart conditions. The PDMS pillars in the cell channel serve as sensors for the beat rate and the heart rhythm. As a proof of principle, it was shown that wild type cells beating in the cell channel deform the micropillars. This deflection, when analyzed yields an alternative method to measure the beat rate of the cardiac tissue as shown in FIGS. 14A-C. Using computational methods the pillar displacement is measured in X and Y direction and the resultant displacement is computed by these two values, The peaks of X, Y, and resultant displacement shown in FIGS. 14A-C correspond to the beating of the 3d microtissue.

Cells

Cells that can be cultured in a microfluidics device of the present disclosure include cardiomyocytes, cardiomyocyte progenitors, induced pluripotent stem (iPS) cells, and the like. In some cases, the cardiomyocytes or cardiomyocyte progenitors are healthy cardiomyocytes or cardiomyocyte progenitors. In some cases, the cardiomyocytes or cardiomyocyte progenitors are diseased cardiomyocytes or cardiomyocyte progenitors. For example, in some cases, the cardiomyocytes or cardiomyocyte progenitors are from an individual having a cardiovascular disease or condition. For example, in some cases, the cardiomyocytes or cardiomyocyte progenitors are from an individual having an ischemic heart disease, an arrhythmia, tachycardia, bradycardia, myocardial infarction, or a congenital heart condition. For example, in some cases, the cardiomyocytes or cardiomyocyte progenitors are from an individual having long QT syndrome (LQTS). Congenital LQTS is an inherited cardiac arrhythmic disease that results from ion channel defects. Drug-induced LQTS can be acquired following use of certain pharmaceutical agents.

Cells that can be cultured in a microfluidics device of the present disclosure include induced pluripotent stem cells (iPS cells). In some cases, the iPS cells are generated from somatic cells obtained from healthy individuals. In some cases, the iPS cells are generated from somatic cells obtained from individuals having a cardiovascular disease or condition. For example, in some cases, the iPS cells are generated from a somatic cell obtained from an individual having a cardiovascular disease or condition such as ischemic heart disease, arrhythmia, tachycardia, bradycardia, myocardial infarction, or a congenital heart condition.

Cardiomyocytes

Cardiomyocytes can have certain morphological characteristics. They can be spindle, round, triangular or multi-angular shaped, and they may show striations characteristic of sarcomeric structures detectable by immunostaining. They may form flattened sheets of cells, or aggregates that stay attached to the substrate or float in suspension, showing typical sarcomeres and atrial granules when examined by electron microscopy Cardiomyocytes and cardiomyocyte precursors generally express one or more cardiomyocyte-specific markers. Cardiomyocyte-specific markers include, but are not limited to, cardiac troponin I (cTnI), cardiac troponin-C, cardiac troponin T (cTnT), tropomyosin, caveolin-3, myosin heavy chain (MHC), myosin light chain-2a, myosin light chain-2v, ryanodine receptor, sarcomeric α-actinin, Nkx2.5, connexin 43, and atrial natriuretic factor (ANF). Cardiomyocytes can also exhibit sarcomeric structures. Cardiomyocytes exhibit increased expression of cardiomyocyte-specific genes ACTC1 (cardiac α-actin), ACTN2 (actinin a2), MYH6 (α-myosin heavy chain), RYR2 (ryanodine receptor 2), MYL2 (myosin regulatory light chain 2, ventricular isoform), MYL7 (myosin regulatory light chain, atrial isoform), TNNT2 (troponin T type 2, cardiac), and NPPA (natriuretic peptide precursor type A), PLN (phospholamban).

In some cases, cardiomyocytes can express cTnI, cTnT, Nkx2.5; and can also express at least 3, 4, 5, or more than 5, of the following: ANF, MHC, titin, tropomyosin, α-sarcomeric actinin, desmin, GATA-4, MEF-2A, MEF-2B, MEF-2C, MEF-2D, N-cadherin, connexin-43, β-1-adrenoreceptor, creatine kinase MB, myoglobin, α-cardiac actin, early growth response-I, and cyclin D2.

In some cases, a cardiomyocyte is generated from an iPS cell, where the iPS cell is generated from a somatic cell obtained from an individual.

Patient-Specific Cells

In some cases, the cells are patient-specific cells. In some cases, the patient-specific cells are derived from stem cells obtained from a patient. In some cases, the patient-specific cells are derived from iPS cells generated from somatic cells obtained from a patient. In some cases, patient-specific cells are primary cells. In some cases, the cells form embryoid bodies (EBs).

Suitable stem cells include embryonic stem cells, adult stem cells, and induced pluripotent stem (iPS) cells.

iPS cells are generated from mammalian cells (including mammalian somatic cells) using, e.g., known methods. Examples of suitable mammalian cells include, but are not limited to: fibroblasts, skin fibroblasts, dermal fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, epithelial cells, gastric epithelial cells, lung epithelial cells, synovial cells, kidney cells, skin epithelial cells, pancreatic beta cells, and osteoblasts.

Mammalian cells used to generate iPS cells can originate from a variety of types of tissue including but not limited to: bone marrow, skin (e.g., dermis, epidermis), muscle, adipose tissue, peripheral blood, foreskin, skeletal muscle, and smooth muscle. The cells used to generate iPS cells can also be derived from neonatal tissue, including, but not limited to: umbilical cord tissues (e.g., the umbilical cord, cord blood, cord blood vessels), the amnion, the placenta, and various other neonatal tissues (e.g., bone marrow fluid, muscle, adipose tissue, peripheral blood, skin, skeletal muscle etc.).

Cells used to generate iPS cells can be derived from tissue or a non-embryonic subject, a neonatal infant, a child, or an adult. Cells used to generate iPS cells can be derived from neonatal or post-natal tissue collected from a subject within the period from birth, including cesarean birth, to death. For example, the tissue source of cells used to generate iPS cells can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

iPS cells produce and express on their cell surface one or more of the following cell surface antigens: SSEA-3, SSEA-4, TRA-1-60, TRA-1-81, TRA-2-49/6E (alkaline phophatase), and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT.

Methods of generating iPS cells are known in the art, and a wide range of methods can be used to generate iPS cells. See, e.g., Takahashi and Yamanaka (2006) Cell 126:663-676; Yamanaka et al. (2007) Nature 448:313-7; Wernig et al. (2007) Nature 448:318-24; Maherali (2007) Cell Stem Cell 1:55-70; Maherali and Hochedlinger (2008) Cell Stem Cell 3:595-605; Park et al. (2008) Cell 134:1-10; Dimos et. al. (2008) Science 321:1218-1221; Blelloch et al. (2007) Cell Stem Cell 1:245-247; Stadtfeld et al. (2008) Science 322: 945-949; Stadtfeld et al. (2008) 2:230-240; Okita et al. (2008) Science 322:949-953.

In some embodiments, iPS cells are generated from somatic cells by forcing expression of a set of factors in order to promote increased potency of a cell or de-differentiation. Forcing expression can include introducing expression vectors encoding polypeptides of interest into cells, introducing exogenous purified polypeptides of interest into cells, or contacting cells with a reagent that induces expression of an endogenous gene encoding a polypeptide of interest.

Forcing expression may include introducing expression vectors into somatic cells via use of moloney-based retroviruses (e.g., MLV), lentiviruses (e.g., HIV), adenoviruses, protein transduction, transient transfection, or protein transduction. In some embodiments, the moloney-based retroviruses or HIV-based lentiviruses are pseudotyped with envelope from another virus, e.g. vesicular stomatitis virus g (VSV-g) using known methods in the art. See, e.g. Dimos et al. (2008) Science 321:1218-1221.

In some embodiments, iPS cells are generated from somatic cells by forcing expression of Oct-3/4 and Sox2 polypeptides. In some embodiments, iPS cells are generated from somatic cells by forcing expression of Oct-3/4, Sox2 and Klf4 polypeptides. In some embodiments, iPS cells are generated from somatic cells by forcing expression of Oct-3/4, Sox2, Klf4 and c-Myc polypeptides. In some embodiments, iPS cells are generated from somatic cells by forcing expression of Oct-4, Sox2, Nanog, and LIN28 polypeptides.

For example, iPS cells can be generated from somatic cells by genetically modifying the somatic cells with one or more expression constructs encoding Oct-3/4 and Sox2. As another example, iPS cells can be generated from somatic cells by genetically modifying the somatic cells with one or more expression constructs comprising nucleotide sequences encoding Oct-3/4, Sox2, c-myc, and Klf4. As another example, iPS cells can be generated from somatic cells by genetically modifying the somatic cells with one or more expression constructs comprising nucleotide sequences encoding Oct-4, Sox2, Nanog, and LIN28.

In some embodiments, cells undergoing induction of pluripotency as described above, to generate iPS cells, are contacted with additional factors which can be added to the culture system, e.g., included as additives in the culture medium. Examples of such additional factors include, but are not limited to: histone deacetylase (HDAC) inhibitors, see, e.g. Huangfu et al. (2008) Nature Biotechnol. 26:795-797; Huangfu et al. (2008) Nature Biotechnol. 26: 1269-1275; DNA demethylating agents, see, e.g., Mikkelson et al (2008) Nature 454, 49-55; histone methyltransferase inhibitors, see, e.g., Shi et al. (2008) Cell Stem Cell 2:525-528; L-type calcium channel agonists, see, e.g., Shi et al. (2008) 3:568-574; Wnt3a, see, e.g., Marson et al. (2008) Cell 134:521-533; and siRNA, see, e.g., Zhao et al. (2008) Cell Stem Cell 3: 475-479.

In some embodiments, iPS cells are generated from somatic cells by forcing expression of Oct3/4, Sox2 and contacting the cells with an HDAC inhibitor, e.g., valproic acid. See, e.g., Huangfu et al. (2008) Nature Biotechnol. 26: 1269-1275. In some embodiments, iPS cells are generated from somatic cells by forcing expression of Oct3/4, Sox2, and Klf4 and contacting the cells with an HDAC inhibitor, e.g., valproic acid. See, e.g., Huangfu et al. (2008) Nature Biotechnol. 26:795-797.

Cardiomyocytes (e.g., patient-specific cardiomyocytes) can be generated from iPS cells using any known method. See, e.g., Mummery et al. (2012) Circ. Res. 111:344.

Under appropriate circumstances, iPS cell-derived cardiomyocytes often show spontaneous periodic contractile activity. This means that when they are cultured in a suitable tissue culture environment with an appropriate $Ca^{n}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between about 6 and 200 contractions per minute, and often between about 20 and about 90 contractions per minute in normal buffer. Individual cells may show spontaneous periodic contractile activity on their own, or they may show spontaneous periodic contractile activity in concert with neighboring cells in a tissue, cell aggregate, or cultured cell mass.

Generation of Cardiomyocytes from iPSCs

Cardiomyocytes can be generated from iPSCs, or other stem cells, using well-known methods/See, e.g., Mummery et al. (2012) *Circ. Res.* 111:344; Lian et al. (2012) *Proc. Natl. Acad. Sci. USA* 109:E1848; Ye et al. (2013) *PLoSOne* 8:e53764.

Generation of Cardiomyocytes Directly from a Post-Natal Somatic Cell

A cardiomyocyte can be generated directly from a post-natal somatic cell, without formation of an iPS cell as an intermediate. For example, in some cases, a human post-natal fibroblast is induced directly (to become a cardiomyocyte, using a method as described in WO 2014/033123. For example, reprogramming factors Gata4, Mef2c, Tbx5, Mesp1, and Essrg are introduced into a human post-natal fibroblast to induce the human post-natal fibroblast to become a cardiomyocyte. In some cases, the polypeptides themselves are introduced into the post-natal fibroblast. In other cases, the post-natal fibroblast is genetically modified with one or more nucleic acids comprising nucleotide sequences encoding Gata4, Mef2c, Tbx5, Mesp1, and Essrg.

Isogenic Pairs of Cardiomyocytes

In some cases, isogenic pairs of cardiomyocytes are used. In some cases, isogenic pairs of wild-type and genetically modified cardiomyocytes are used. In some cases, isogenic pairs of diseased and non-diseased cardiomyocytes are used. For example, in some cases, isogenic pairs of cardiomyocytes from an individual are used, where one of the isogenic pair is genetically modified with a nucleic acid comprising a nucleotide sequence encoding a mutant form of a polypeptide such that the genetically modified cardiomyocyte exhibits characteristics of a diseased cardiomyocyte.

In some cases, isogenic pairs of iPS cells are used. In some cases, isogenic pairs of wild-type and genetically modified iPS cells are used. In some cases, isogenic pairs of diseased and non-diseased iPS cells are used.

Genetic Modification

In some cases, a cardiomyocyte or cardiomyocyte precursor, or iPS cell, is genetically modified. For example, a cardiomyocyte, cardiomyocyte precursor, or iPS cell, can be genetically altered to express one or more growth factors of various types such as FGF, cardiotropic factors such as atrial natriuretic factor, cripto, and cardiac transcription regulation factors, such as GATA-4, Nkx2.5, and MEF2-C. Genetic modification generally involves introducing into the cardiomyocyte, cardiomyocyte precursor, or iPS cell a nucleic acid comprising a nucleotide sequence encoding a polypeptide of interest. The nucleotide sequence encoding the polypeptide of interest can be operably linked to a transcriptional control element, such as a promoter. Suitable promoters include, e.g., promoters of cardiac troponin I (cTnI), cardiac troponin T (cTnT), sarcomeric myosin heavy chain (MHC), GATA-4, Nkx2.5, N-cadherin, .beta.1-adrenoceptor, ANF, the MEF-2 family of transcription factors, creatine kinase MB (CK-MB), myoglobin, or atrial natriuretic factor (ANF).

In some cases, a cardiomyocyte is genetically modified with a nucleic acid comprising a nucleotide sequence encoding a mutant form of a polypeptide such that the genetically modified cardiomyocyte exhibits characteristics of a diseased cardiomyocyte. For example, a cardiomyocyte can be genetically modified to express a KVLQT1, HERG, SCN5A, KCNE1, or KCNE2 polypeptide comprising a mutation associated with LQTS, where the genetically modified cardiomyocyte exhibits characteristics associated with LQTS. See, e.g., Splawski et al. (2000) Circulation 102:1178, for mutations in KVLQT1, HERG, SCNSA, KCNE1, and KCNE2 that are associated with LQTS. For example, a cardiomyocyte can be genetically modified such that a gene encoding a KVLQT1, HERG, SCNSA, KCNE1, or KCNE2 polypeptide with a LQTS-associated mutation replaces a wild-type KVLQT1, HERG, SCNSA, KCNE1, or KCNE2 gene.

In some cases, a cardiomyocyte is genetically modified to express a genetically-encoded calcium indicator (GECI). See, e.g., Mank and Griesbeck (2008) *Chem. Rev.* 108:1550; Nakai et al. (2001) *Nat. Biotechnol.* 19:137; Akerboom et al. (2012) *J. Neurosci.* 32:13819; Akerboom et al. (2013) *Front. Mol. Neurosci.* 6:2. Suitable GECI include pericams, cameleons (Miyawaki et al (1999) *Proc. Natl. Acad. Sci. USA* 96:2135), and GCaMP. As one non-limiting example, a suitable GECI can be a fusion of a circularly permuted variant of enhanced green fluorescent protein (cpEGFP) with the calcium-binding protein calmodulin (CaM) at the C terminus and a CaM-binding M13 peptide (from myosin light chain) at the N terminus. Nakai et al. (2001) *Nat. Biotechnol.* 19:137. In some cases, a suitable GECI can comprise an amino acid sequence having at least 85%, at least 90%, at least 95%, at least 98%, or 100%, amino acid sequence identity with the following GCaMP6 amino acid sequence:

```
                                                      (SEQ ID NO: //)
mgshhhhhhg masmtggqqm grdlyddddk dlatmvdssr rkwnktghav raigrlssle nvyikadkqk ngikanfkir hniedggvql ayhyqqntpi gdgpvllpdn hylsvqskls kdpnekrdhm vllefvtaag itlgmdelyk ggtggsmvsk geelftgvvp ilveldgdvn ghkfsysgeg egdatygklt lkficttgkl pvpwptlvtt lxvqcfsryp dhmkqhdffk sampegyiqe rtiffkddgn yktraevkfe gdtlvnriel kgidfkedgn ilghkleynl pdqlteeqia efkeafslfd kdgdgtittk elgtvmrslg qnpteaelqd minevdadgd gtidfpeflt mmarkgsyrd teeeireafg vfdkdgngyi saaelrhvmt nlgekltdee vdemireadi dgdgqvnyee fvqmmtak
```

Methods for Culturing Cells

Aspects of the disclosure include methods for culturing cells using the subject devices and systems. In some embodiments, the methods involve introducing a plurality of cells into the cell culture channel of a device, and introducing a cell culture medium into the media channels of the device. Once the cells have been introduced into the device, the subject methods involve maintaining the device under suitable cell culture conditions. In some embodiments, the cell culture conditions include a controlled temperature that ranges from 30° C. to 40° C., such as from 35° C. to 38° C. In some embodiments, the cell culture conditions include a controlled $CO_2$ gas concentration ranging from 2% to 10%, such as 4% to 6%. In some embodiments, the cell culture conditions include a controlled humidity environment to reduce evaporative loss of cell culture medium.

The subject methods involve moving the cell culture medium through the media channels of the device and allowing the cell culture medium to pass through the micro channels that connect the media channels to the cell culture channel. In some embodiments, the cell culture medium is moved through the media channels of the device using gravity or using applied positive or negative pressure.

In some embodiments, the methods involve introducing a plurality of cells and a cell culture medium into the device, as described above, and maintaining the device under suitable cell culture conditions for a period of time that ranges from one day to one month. In certain embodiments, the methods involve removing a plurality of cells from the device after a specified period of time has elapsed. For example, in some embodiments, a plurality of cells may be cultured in the device for a period of time ranging from one day to one month, and the cells may then be removed from the device.

In some embodiments, the methods involve collecting data from the cells in the device during the culture process using one or more sensors. Data may be collected at any desired point in time during the culture process. In some embodiments, data may be collected at regular intervals during the culture process, e.g., may be collected on an hourly or a daily basis.

In certain embodiments, a sensor in the device is a mechanosensing pillar, and the methods involve measuring data from the cells in the device during the culture process by measuring the deflection or displacement of the mechanosensing pillar in response to forces that are exerted on the pillar by the cells in the device. In some embodiments, the methods involve measuring a beat rate and/or a rhythm of the cells in the device. In some embodiments, a sensor in the device is an electrode, and the methods involve measuring data from the cells in the device during the culture process by measuring a voltage potential of the electrode. The voltage potential of the electrode can be used to determine the electrical activity of the cells in the device. In some embodiments, the electrical activity of the cells can be measured as a function of time to determine, e.g., a beat rate and/or a rhythm of the cells that are cultured in the device.

In some embodiments, the methods include manipulating the subject microfluidic device to introduce a constraint on the cell culture process that can be used to simulate a disease state. For example, in some embodiments the methods involve interrupting and/or reducing the amount of a nutrient and/or oxygen that is delivered to the cells from a media channel. As provided above, a cell culture medium flows from each of the two media channels into the cell culture channel, where it delivers nutrients and oxygen to the cells. In some embodiments, the methods involve simulating a disease state by restricting the flow of the cell culture medium through the device, thereby reducing the delivery of nutrients to the cells. In certain embodiments, the methods involve completely or partially blocking one or both of the media channels to reduce the flow of the cell culture media to the cells. The effects of the reduced delivery of nutrients and/or oxygen to the cells can then be evaluated, e.g., using the sensors. The methods can be used to simulate any disease state that involves reduced nutrient and/or oxygen delivery to cells.

Computer Programs

Aspects of the subject systems include a controller, a processor and a computer readable medium that are configured or adapted to operate one or more components of the subject systems and/or devices. In some embodiments, a system includes a controller that is in communication with one or more components of the devices or systems, as described herein, and is configured to control aspects of the devices or systems and/or execute one or more operations or functions of the subject devices or systems. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein.

In some embodiments, a system includes a user interface, such as a graphical user interface (GUI), that is adapted or configured to receive input from a user, and to execute one or more of the methods as described herein. In some embodiments, a GUI is configured to display data or information to a user.

Utility

A microfluidics device of the present disclosure is useful for a variety of applications, including, but not limited to, drug screening; determining the potential effect of a drug on an individual; drug toxicity testing; and research applications, such as characterization of patient-specific cell populations.

Drug Screening Methods

The present disclosure provides drug screening methods for identifying a candidate agent that modulates a characteristic of a plurality of cells. The methods generally involve: a) introducing a plurality of cells into the cell culture channel of a cell culture device of the present disclosure; b) introducing a cell culture medium into the media channels of the device; c) contacting the cells with the candidate agent; d) maintaining the device under suitable cell culture conditions; and e) measuring a characteristic of the cells using the sensor. A change in the characteristic of the cells in the presence of the candidate agent compared to a characteristic of the cells in the absence of the candidate agent indicates that the candidate agent has use in modulating the characteristic of the cells. Such methods are useful for, e.g., identifying a candidate agent for treating a cardiac condition or disease.

In some cases, the cells used in a subject drug screening method comprise cardiomyocytes, where cardiomyocytes can be any of the cardiomyocytes as described hereinabove. For example, in some cases, the cardiomyocytes exhibit one or more characteristics of a cardiac disease or condition (a cardiac abnormality). For example in some cases, the cardiomyocytes exhibit one or more characteristics of ischemic heart disease, arrhythmia, tachycardia, bradycardia, myocardial infarction, or a congenital heart condition.

In some cases, the cells used in a subject drug screening method comprise stem cells. In some cases, the cells used in a subject drug screening method comprise induced pluripotent stem cells. In some cases, the cells used in a subject drug screening method are human cells, e.g., human cardiomyocytes, human cardiomyocyte precursors (progenitors), or human iPS cells.

In some cases, the sensor in a device used in a method of the present disclosure comprises a mechanosensing pillar, and the step of measuring a characteristic of the cells comprises measuring a beat rate and/or a rhythm of the cells by measuring a deflection of the mechanosensing pillar.

In some cases, the sensor in a device used in a method of the present disclosure comprises an electrode, and the step of measuring a characteristic of the cells comprises measuring a beat rate and/or a rhythm of the cells by measuring a voltage potential of the electrode.

In some instances, a method of the present disclosure for identifying a candidate agent that modulates a characteristic of a plurality of cells comprises: a) introducing a plurality of stem cells into the cell culture channel of a cell culture device of the present disclosure; b) differentiating the cells into a lineage; c) introducing a cell culture medium into the media channels of the device; d) contacting the cells with the candidate agent; e) maintaining the device under suitable cell culture conditions; and f) measuring a characteristic of the cells using the sensor.

In some cases, the cells used in a subject drug screening method are genetically modified cells. In some cases, the method involves genetically modifying the cells after the cells have been introduced into the cell culture channel of the cell culture device.

In some instances, a method of the present disclosure for identifying a candidate agent that modulates a characteristic of a plurality of cells further comprises blocking at least one of the media channels of the device to simulate a disease state by reducing an amount of a nutrient and/or an amount of oxygen that is delivered to the cells from the media channel. For example, in some cases, a method of the present disclosure for identifying a candidate agent that modulates a characteristic of a plurality of cells comprises: a) introducing a plurality of cells into the cell culture channel of a cell culture device of the present disclosure; b) introducing a cell culture medium into the media channels of the device; c) blocking at least one of the media channels of the device to simulate a disease state by reducing an amount of a nutrient and/or an amount of oxygen that is delivered to the cells from the media channel; d) contacting the cells with the candidate agent; e) maintaining the device under suitable cell culture conditions; and f) measuring a characteristic of the cells using the sensor.

In some instances, a method of the present disclosure for identifying a candidate agent that modulates a characteristic of a plurality of cells further comprises modulating a dimension of the device to simulate a disease state by reducing an amount of a nutrient and/or an amount of oxygen that is delivered to the cells from the media channel. For example, in some cases, a method of the present disclosure for identifying a candidate agent that modulates a characteristic of a plurality of cells comprises: a) introducing a plurality of cells into the cell culture channel of a cell culture device of the present disclosure; b) introducing a cell culture medium into the media channels of the device; c) modulating a dimension of the device to simulate a disease state by reducing an amount of a nutrient and/or an amount of oxygen that is delivered to the cells from the media channel; d) contacting the cells with the candidate agent; e) maintaining the device under suitable cell culture conditions; and f) measuring a characteristic of the cells using the sensor. For example, in some cases, the dimension of the device that is modulated is the width of the cell culture channel.

As discussed above, in some cases, the cardiomyocytes exhibit one or more characteristics of a cardiac disease or condition. For example, in some cases, the cardiomyocytes are obtained from an individual having a cardiac disease or condition, or are generated from somatic cells from an individual having a cardiac disease or condition, or are generated from iPS cells generated from somatic cells from an individual having a cardiac disease or condition. In some cases, the cardiomyocytes are genetically modified such that the genetically modified cardiomyocyte exhibits one or more characteristics of a cardiac disease or condition. In some cases, isogenic cardiomyocytes, as described above, are used.

Drugs or test agents may be individual small molecules of choice (e.g., a lead compound from a previous drug screen) or in some cases, the drugs or test agents to be screened come from a combinatorial library, e.g., a collection of diverse chemical compounds generated by either chemical synthesis or biological synthesis by combining a number of chemical "building blocks." For example, a linear combinatorial chemical library such as a polypeptide library is formed by combining a set of amino acids in every possible way for a given compound length (e.g., the number of amino acids in a polypeptide compound). Millions of test agents (e.g., chemical compounds) can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al. (1994), J. Med. Chem 37(9), 1233. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al. (1993), Proc. Natl. Acad. Sci. U.S.A. 90, 6909; analogous organic syntheses of small compound libraries, as described in Chen et al. (1994), J. Amer. Chem. Soc., 116: 2661; Oligocarbamates, as described in Cho, et al. (1993), Science 261, 1303; peptidyl phosphonates, as described in Campbell et al. (1994), J. Org. Chem., 59: 658; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

In some embodiments, a cardiomyocyte or cardiac progenitor is contacted with a test agent in a subject device, as described above, and the effect, if any, of the test agent on a biological activity of the cardiomyocyte or cardiac progenitor is assessed, where a test agent that has an effect on a biological activity of the cardiomyocyte or cardiac progenitor is a candidate agent for treating a cardiac disorder or condition. For example, a test agent of interest is one that increases a biological activity of the cardiomyocyte or cardiac progenitor by at least about 5%, at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the biological activity in the absence of the test agent. A test agent of interest is a candidate agent for treating a cardiac disorder or condition.

A "biological activity" includes, e.g., one or more of marker expression (e.g., cardiomyocyte-specific marker expression), receptor binding, ion channel activity, contractile activity, and electrophysiological activity.

For example, in some embodiments, the effect, if any, of the test agent on expression of a cardiomyocyte marker is assessed. Cardiomyocyte markers include, e.g., cardiac troponin I (cTnI), cardiac troponin T (cTnT), sarcomeric myosin heavy chain (MHC), GATA-4, Nkx2.5, N-cadherin, β-adrenoceptor (β1-AR), a member of the MEF-2 family of transcription factors, creatine kinase MB (CK-MB), myoglobin, and atrial natriuretic factor (ANF).

As another example, the effect, if any, of the test agent on electrophysiology of the cardiomyocyte or cardiac progenitor is assessed.

As another example, in some embodiments, the effect, if any, of the test agent on ligand-gated ion channel activity is assessed. As another example, in some embodiments, the effect, if any, of the test agent on voltage-gated ion channel activity is assessed. The effect of a test agent on ion channel activity is readily assessed using standard assays, e.g., by measuring the level of an intracellular ion (e.g., $Na^+$, $Ca^{2+}$, $K^+$, etc.). A change in the intracellular concentration of an ion can be detected using an indicator (e.g., a chemical indicator; a genetically encoded indicator) appropriate to the ion whose influx is controlled by the channel. For example, where the ion channel is a potassium ion channel, a potassium-detecting dye is used; where the ion channel is a calcium ion channel, a calcium-detecting dye is used; etc. As noted above, a genetically encoded calcium indicator can be used.

Suitable intracellular $K^+$ ion-detecting dyes include, but are not limited to, $K^+$-binding benzofuran isophthalate and the like.

Suitable intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., *Methods in Cell Biology, Volume 40: A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999); *Calcium Signaling Protocols* (Methods in Molecular Biology), 2005, D. G. Lamber, ed., Humana Press.)

In some embodiments, screening of test agents is conducted using cardiomyocytes or cardiac progenitors that display an abnormal cellular phenotype (e.g., abnormal cell morphology, gene expression, or signaling), associated with a health condition or a predisposition to the health condition (e.g., a cardiac condition). Such assays may include contacting a test population of cardiomyocytes or cardiac progenitors (e.g., generated from one or more iPS donors exhibiting a cardiac disease or condition) with a test compound; and contacting with a negative control compound a negative control population of cardiomyocytes or cardiac progenitors (e.g., generated from one or more iPS donors exhibiting the cardiac disease or condition). The assayed cellular phenotype associated with the cardiac disease or condition of interest in the test and negative control populations can then be compared to a normal cellular phenotype. Where the assayed cellular phenotype in the test population is determined as being closer to a normal cellular phenotype than that exhibited by the negative control population, the drug candidate compound is identified as normalizing the phenotype.

The effect of a test agent in the assays described herein can be assessed using any standard assay to observe phenotype or activity of cardiomyocytes or cardiac progenitors, such as marker expression, receptor binding, contractile activity, or electrophysiology. For example, in some cases, pharmaceutical candidates are tested for their effect on contractile activity, such as whether they increase or decrease the extent or frequency of contraction. Where an effect is observed, the concentration of the compound can be titrated to determine the half-maximal effective dose (ED50).

Test Agent/Drug Toxicity

A method of the present disclosure can be used to assess the toxicity of a test agent, or drug, e.g., a test agent or drug designed to have a pharmacological effect on cardiac progenitors or cardiomyocytes, e.g., a test agent or drug designed to have effects on cells other than cardiac progenitors or cardiomyocytes but potentially affecting cardiac progenitors or cardiomyocytes as an unintended consequence. In some embodiments, the disclosure provides methods for evaluating the toxic effects of a drug, test agent, or other factor, in a human or non-human (e.g., murine; lagomorph; non-human primate) subject, comprising contacting one or more cardiomyocytes or cardiac progenitors with a dose of a drug, test agent, or other factor and assaying the contacted cardiac progenitor cells and/or cardiomyocytes for markers of toxicity or cardiotoxicity; for effects of the drug on mechanical properties, such as contractility, of the cardiomyocytes; or for effects of the drug on electrical properties of the cardiomyocytes.

Any method known in the art may be used to evaluate the toxicity or adverse effects of a test agent or drug on cardiomyocytes or cardiac progenitors. Cytotoxicity or cardiotoxicity can be determined, e.g., by the effect on cell viability, survival, morphology, and the expression of certain markers and receptors. For example, biochemical markers of myocardial cell necrosis (e.g., cardiac troponin T and I (cTnT, cTnI)) may be used to assess drug-induced toxicity or adverse reactions in cardiomyocytes or cardiac progenitors, where the presence of such markers in extracellular fluid (e.g., cell culture medium) can indicate necrosis. See, e.g., Gaze and Collinson (2005) Expert Opin Drug Metab Toxicol 1(4):715-725. In another example, lactate dehydrogenase is used to assess drug-induced toxicity or adverse reactions in cardiomyocytes or cardiac progenitors. See, e.g., Inoue et al. (2007) AATEX 14, Special Issue: 457-462. In another example, the effects of a drug on chromosomal DNA can be determined by measuring DNA synthesis or repair and used to assess drug-induced toxicity or adverse reactions in cardiomyocytes or cardiac progenitors. In still another example, the rate, degree, and/or timing of [$^3$H]-thymidine or BrdU incorporation may be evaluated to assess drug-induced toxicity or adverse reactions in cardiomyocytes or cardiac progenitors. In yet another example, evaluating the rate or nature of sister chromatid exchange, determined by metaphase spread, can be used to assess drug-induced toxicity or adverse reactions in cardiomyocytes or cardiac progenitors. See, e.g., A. Vickers (pp 375-410 in In vitro Methods in Pharmaceutical Research, Academic Press, 1997). In yet another example, assays to measure electrophysiology or activity of ion-gated channels (e.g., Calcium-gated channels) can be used to assess drug-induced toxicity or adverse reactions in cardiomyocytes or cardiac progenitors. In still another example, contractile activity (e.g., frequency of contraction) can be used to assess drug-induced toxicity or adverse reactions in cardiomyocytes or cardiac progenitors.

Thus, the present disclosure provides a method of evaluating an effect of an agent on a plurality of cells, the method comprising: a) introducing a plurality of cells into the cell culture channel of a cell culture device of the present disclosure; b) introducing a cell culture medium into the media channels of the device; c) contacting the cells with the agent; d) maintaining the device under suitable cell culture conditions; and e) measuring a characteristic of the cells using the sensor. A change in the characteristic of the cells in the presence of the agent compared to a characteristic of the cells in the absence of the agent indicates that the agent modulates the characteristic of the cells. Characteristics include mechanical characteristics, such as contractility; and electrical characteristics such as voltage potential across a cell membrane.

In some cases, the cells used in a subject method of evaluating an effect of an agent on a plurality of cells comprise cardiomyocytes, where cardiomyocytes can be any of the cardiomyocytes as described hereinabove. For example, in some cases, the cardiomyocytes exhibit one or more characteristics of a cardiac disease or condition (a cardiac abnormality). For example in some cases, the cardiomyocytes exhibit one or more characteristics of ischemic heart disease, arrhythmia, tachycardia, bradycardia, myocardial infarction, or a congenital heart condition.

In some cases, the cells used in a subject method of evaluating an effect of an agent on a plurality of cells comprise stem cells. In some cases, the cells used in a subject method of evaluating an effect of an agent on a plurality of cells comprise induced pluripotent stem cells. In some cases, the cells used in a subject method of evaluating an effect of an agent on a plurality of cells are human cells, e.g., human cardiomyocytes, human cardiomyocyte precursors (progenitors), or human iPS cells.

In some cases, the sensor in the device used in a subject method of evaluating an effect of an agent on a plurality of cells comprises a mechanosensing pillar, and the evaluating step comprises measuring a characteristic of the cells comprises measuring a beat rate and/or a rhythm of the cells by measuring a deflection of the mechanosensing pillar.

In some cases, the sensor in the device used in a subject method of evaluating an effect of an agent on a plurality of cells comprises an electrode, and the evaluating step comprises measuring a characteristic of the cells comprises measuring a beat rate and/or a rhythm of the cells by measuring a voltage potential of the electrode.

In some cases, the method comprises differentiating the cells (e.g., stem cells, such as iPS cells) into a lineage, e.g., a cardiomyocyte lineage. Stems cells (e.g., iPS cells) can be induced to become cardiomyocytes before being introduced into (loaded into) a device of the present disclosure. Stems cells (e.g. iPS cells) can be induced to become cardiomyocytes when the stem cells (e.g., iPS cells) are already loaded in a device of the present disclosure.

In some cases, the method further comprises genetically modifying the cells.

In some cases, the method further comprises blocking at least one of the media channels of the device to simulate a disease state by reducing an amount of a nutrient and/or an amount of oxygen that is delivered to the cells from the media channel.

In some cases, the method further comprises modulating a dimension of the device to simulate a disease state by reducing an amount of a nutrient and/or an amount of oxygen that is delivered to the cells from the media channel. In some instances, the device that is modulated is the width of the cell culture channel.

In some embodiments, the present disclosure provides methods for reducing the risk of drug toxicity in a human or murine subject, comprising contacting one or more cardiomyocytes or cardiac progenitors with a dose of a drug, test agent, or pharmacological agent, assaying the contacted one or more differentiated cells for toxicity, and prescribing or administering the pharmacological agent to the subject if the assay is negative for toxicity in the contacted cells. In some embodiments, the present disclosure provides methods for reducing the risk of drug toxicity in a human or murine subject, comprising contacting one or more cardiomyocytes or cardiac progenitors with a dose of a pharmacological agent, assaying the contacted one or more differentiated cells for toxicity, and prescribing or administering the pharmacological agent to the subject if the assay indicates a low risk or no risk for toxicity in the contacted cells.

Predicting Patient Response

The present disclosure provides methods for predicting patient response to a drug, the method generally involving a) introducing a plurality of cells (e.g., cardiomyocytes; cardiomyocyte progenitors; iPS cells) into the cell culture channel of a cell culture device of the present disclosure; b) introducing a cell culture medium into the media channels of the device; c) contacting the cells with the drug; d) maintaining the device under suitable cell culture conditions; and e) measuring a characteristic of the cells using the sensor. A change in the characteristic of the cells in the presence of the drug compared to a characteristic of the cells in the absence of the drug indicates that the drug modulates the characteristic of the cells. In some cases, the method further comprises preparing a report indicating that: i) the drug exhibited an undesirable effect on one or more cardiomyocyte characteristics; ii) the drug exhibited no detectable undesirable effects on one or more cardiomyocyte characteristics; or iii) further evaluation of the drug is required. In some cases, e.g., there the report indicates that the drug exhibited an undesirable effect on one or more cardiomyocyte characteristics, the method could further include preparing a report recommending that: i) use of the drug be discontinued in the patient from whom the cardiomyocytes were obtained and to whom the drug has been administered; or ii) the drug not be administered to the patient from whom the cardiomyocytes were obtained.

The following are non-limiting examples of uses of a biomimetic device of the present disclosure.

1. Drug Screening System for Toxicology Studies:

There is an urgent need in pharmaceutical industry to effectively and efficiently screen potential drug compounds during early stages to assess both effectiveness and toxicity. The present physiologically functioning integrated cardiac system can be used for drug compound on a subset of patients. This is relevant to determine pharmacokinetics and pharmacodynamics for patients, e.g., with patient having rare genetic disorders, as addressing this issue truly moves drug discovery and development into the era of personalized medicine. The present devices can be used for on-chip differentiation of hiPSCs into various lineages. Furthermore, the MCG can be used as alternative to for diagnosing various cardiac abnormalities.

2. On Chip Differentiation and MCG as a Tool for Personalized Medicine.

Figure 16:
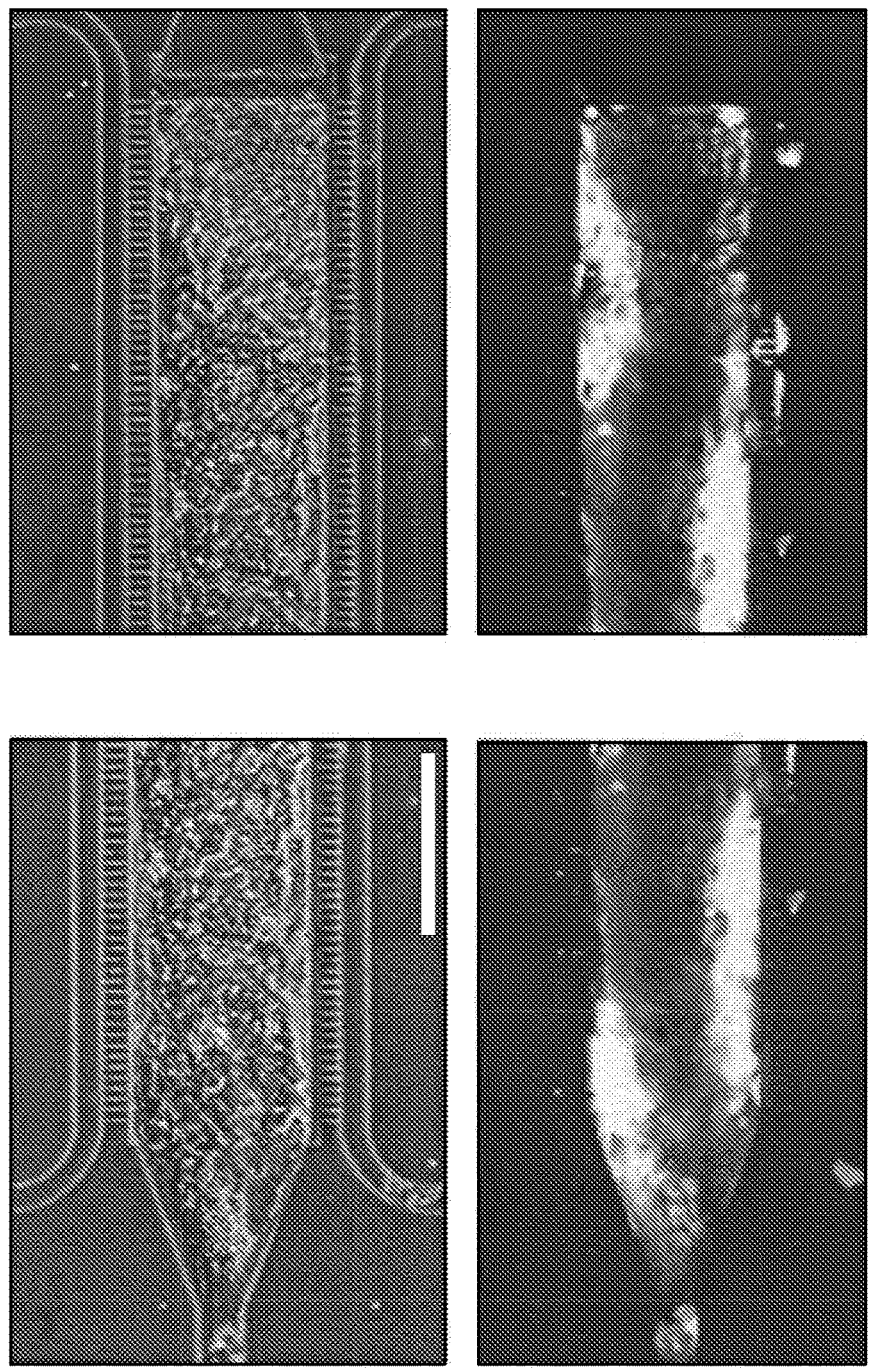
FIG. 16 depicts monitoring of cell viability in a device of the present disclosure.

A major need of the pharmaceutical industry is to ascertain the effects of a drug compound on a subset of patients. This is relevant to determine pharmacokinetics and pharmacodynamics for patients, e.g., with patient having rare genetic disorders. A subject device can be used for on-chip differentiation of hiPSCs into various lineages as shown in FIG. 16. Furthermore, the MCG can be used as alternative to for diagnosing various cardiac disorders.

3. Model/Create Diseased Tissues In Vitro

To recapitulate human disease states it is of upmost importance to generate in vitro disease-specific model tissues. The presented device is capable of achieving this using two different approaches:

(i) Disease-specific cardiomyocytes (CMs) can either be directly loaded into the device or generated by differentiation of human disease-specific iPS cells on-chip. Thereby, a disease-specific model tissue is created.

(ii) The device can be used to simulate various types of tissue/cell injury and test various drugs for that disorder. One such example is the modeling of cardiac ischemia, which occurs when blood flow to the heart muscle is decreased by a partial or complete blockage of heart's arteries. The decrease in blood flow reduces heart's oxygen supply. Ischemia can be modeled in two ways:

(a) Block one of the media channels that deliver nutrients and oxygen to the cell culture channel.

(b) Decrease the oxygen supply to the micro tissue by increasing the device thickness.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Differentiation of Healthy and LQTS hiPS Cells into Cardiomyocytes

Cardiomyocytes were generated from multiple iPSCs, including healthy WT iPSCs, patient-derived LQT3 diseased iPSCs, and the isogenic GCaMP6 iPS cell line. According to fluorescence activated cell sorting (FACS) results, more than 75%, and typically greater than 85%, human cardiomyocytes were obtained from multiple iPS cell lines, including the healthy WT iPSCs, patient-derived LQT3 diseased iPSCs, and the isogenic GCaMP6 iPS cell line. GCaMP6 is a genetically encoded calcium indicator (GECI) protein; and is a fusion of a circularly permuted variant of enhanced green fluorescent protein (cpEGFP) with the calcium-binding protein calmodulin (CaM) at the C terminus and a CaM-binding M13 peptide (from myosin light chain) at the N terminus. Nakai et al. (2001) *Nat. Biotechnol.* 19:137; and Akerboom et al. (2012) *J. Neurosci.* 32:13819.

For dynamic calcium imaging measurements, GCaMP6 hiPSC-CMs were used. The use of this CM line and technique can be used as an alternative to invasive electrophysiology measurements, such as patch clamp measurements, and does not require any special substrate or fluorescent dye (FIGS. 1A-B).

FIG. 1. Cardiac tissue derived from a genetically engineered hiPS cell expressing a GCaMP6 reporter in the NIPS: (A) Frames from a fluorescence movie (GFP channel) showing the switching from dim to bright during activity of Ca2+ channels. (B) Time-course of the normalized fluorescence intensity (right y-axis) and the beating motion (left y-axis) obtained by computational analysis of the movie. The line scans are offset for clarity, where the lower trace reflects the beating velocity and the upper trace reflects the normalized fluorescence intensity. This combination allows high throughput analysis of mechanical (beating velocity) and electrophysiological ($Ca^{2+}$ transient) properties.

The fluorescence intensity of the calcium transient from GCaMP6 hiPSC-CMs was closely correlated with the action potential recording using sharp electrode. Thus, GCaMP6 hiPSC-CMs were a powerful non-invasive platform for the in vitro analysis of the electrophysiology of a human cardiac tissue model during drug screening and toxicity testing. The GCaMP6 hiPSC line is useful for any physiological process where calcium levels are altered, such as in cardiac muscle contraction.

Example 2: Development of a Cardiac Microphysiological System (MPS) as a Microfluidic 3D In Vitro Model of the Human Myocardium A cardiac MPS that incorporates an in vitro 3D model of the human myocardium consisting of aligned CMs derived from hiPS cells was designed, fabricated and characterized with various in and ex situ monitoring tools. The MPS organized the structure of healthy and LQTS hiPSC-CMs into a 3D in vitro model of the human myocardium. The engineered cardiac tissue was robust and beat spontaneously at physiological beat rates. The device allowed for continuous monitoring (sensing), sampling (testing and continuous data collection and analysis), and probing (direct in-cell measurements) of the cardiac tissue model. To characterize the functionality of the cardiac model, a motion tracking method capable of massive parallelization and high throughput analysis based on bright field microscopy as well as a custom made MEA enabling electrophysiological measurements inside the MPS was developed.

Design of the MPS Microfluidic Device

The MPS microfluidic device allows for a precise and highly controlled delivery of compounds (nutrients, hormones, drugs). Components of the device include a central cell chamber and two adjacent media channels (FIG. 2, panels A, B).

FIG. 2. Schematic design (A) and scanning electron microscopy (SEM) image (B) of the cardiac MPS featuring a central cell channel and adjacent media channels. The zoom-in highlights the connecting perfusion barriers, which are shown red in (A). (C) Optical microscopy image of a cardiac tissue in the MPS consisting of hiPSC derived cardiomyocytes. (D) Confocal fluorescence microscopy image of a stained 3D cardiac tissue inside the MPS revealing the preferred alignment of the single cells along the channel axis. (E) Motion tracking characterization showing distinct contraction and relaxation peaks. The tissue beat spontaneously and at physiological beat rates.

Figure 3:
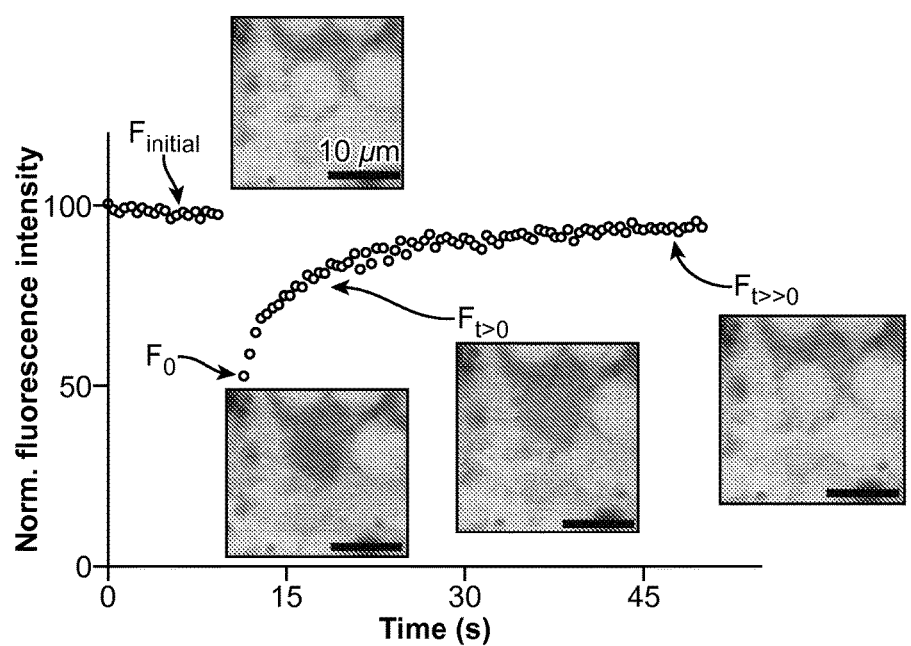
FIG. 3 depicts the diffusion dynamics in a microphysiological system (MPS) of the present disclosure.

The dimensions of the cell chamber reproduced the perimysial collagen fiber spacing in the human heart (100 µm-200 µm). The cell chamber was connected to the media channels by small microchannels (width/height 2 µm) that allow perfusion from the media channels to the cell chamber. Due to the high fluidic resistance, the nutrient and drug transport from the media channels to the cell chamber was purely diffusive and thereby stresses due to shear flow on the cells/tissue were minimized. Moreover, the perfusion system mimicked the human in vivo situation by resembling the diffusive properties of the endothelial barrier. Diffusive transport through the endothelial-like barrier channels was confirmed using flow experiments with fluorescence FITC-dextran probes and fluorescence recovery after photobleaching (FRAP) and the characteristic diffusion time was determined to be 2.5 s (FIG. 3A). Additionally a sufficient supply with oxygen was confirmed by COMSOL simulations (FIG. 3).

FIG. 3. Diffusion dynamics in the microphysiological system. Normalized fluorescence recovery of 4 kDa FITC—dextran (0.2 mg/mL). Insets are confocal microscopy images corresponding to the FRAP experiment. $F_{initial}$ is the time regime that corresponds to the initial fluorescence before bleaching; F0 is the fluorescence measurement immediately after photobleaching; Ft>0 corresponds to the recovery of fluorescence after photobleaching; F t>>0 corresponds to maximal recovery of fluorescence at the end of the experiment.

Characterization of the MPS Microfluidic Device

By optimizing cell injection parameters and the cell singularization process, cells were loaded at a high packing density using low stress and pressure. The loaded cell mixture subsequently formed a 3D cardiac tissue within 24 hours after loading and started to beat spontaneously (FIG. 2, panel C). The spontaneous beating was homogeneous and at physiological beat rates (55 bpm-80 bpm) without pacing and in serum-free medium (FIG. 2, panel E). Physiological baseline beating was crucial as drug response in 2D culture depends strongly on the initial beat rate. Moreover, the cardiac tissue had an aligned structure and an aligned beating motion (FIG. 2, panel D and FIGS. 4A-C).

Figure 4:
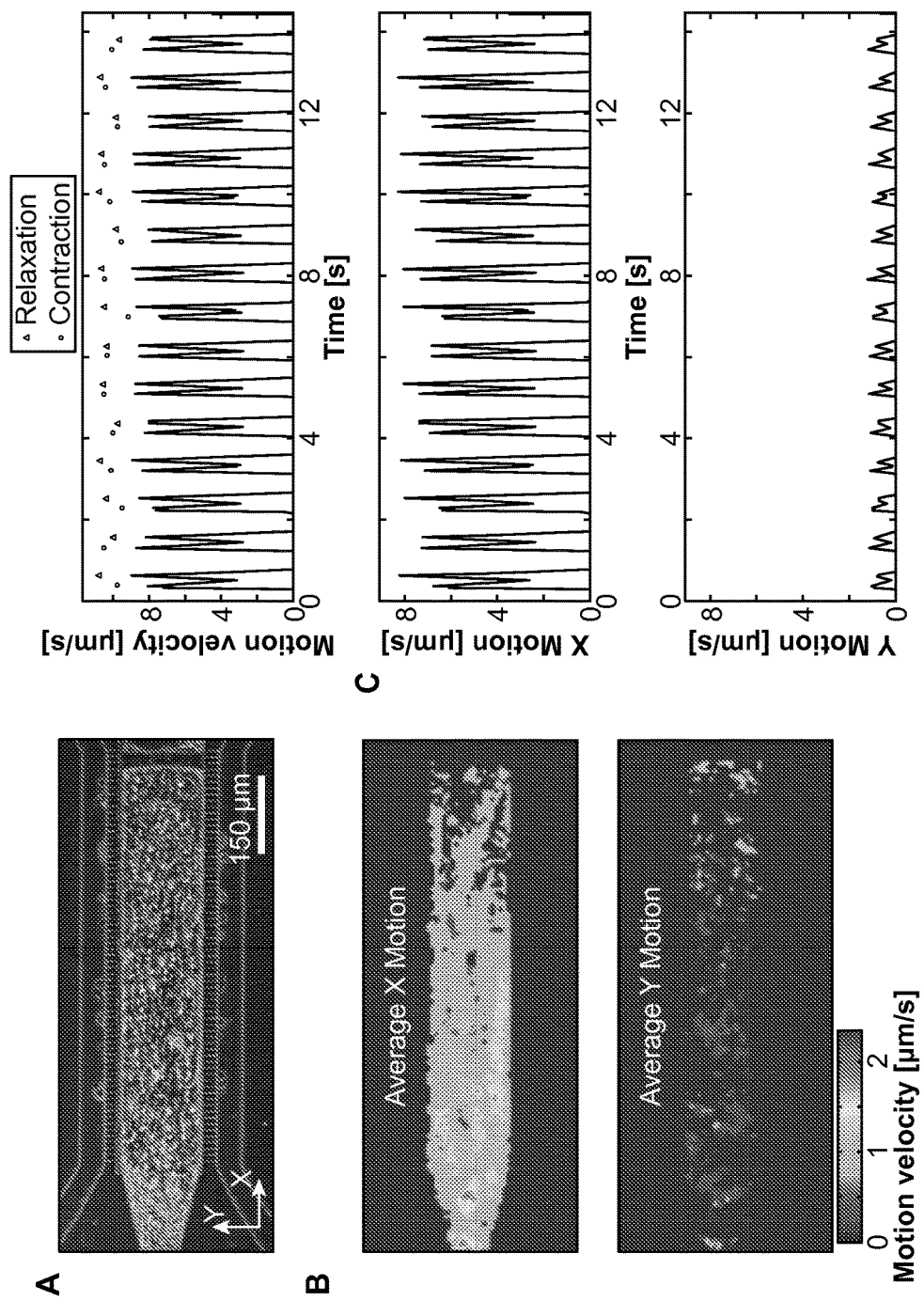
FIGS. 4A-C depict a cardiac tissue consisting of WTC hiPSC-CMs in an MPS and its beating motion determined by motion tracking, according to an embodiment of the present disclosure.

FIG. 4. (A) Optical microscopy image of a cardiac tissue in the MPS consisting of WTC hiPSC-CMs. The tissue beats spontaneously and at physiological beat rates, which could be monitored using the motion tracking method (Tracings on the Right). The motion tracking also allowed the characterization of the direction of the beating: (B) Heat map of the time averaged beating motion along (top) and perpendicular (bottom) to the channel axis. (C) Kinetics of the beating motion along (top) and perpendicular (bottom) to the channel axis.

When fed continuously the tissue remained viable and functional for more than one month. Healthy and LQTS hiPSC-CM-derived cardiac tissue in the MPS were viable and amenable to continuous monitoring (e.g., MEA) and sampling for over 4 weeks. Beating tissues were created and loaded from multiple iPS cell lines, a disease cell line (LQT3), and the GCaMP6 isogenic reporter cell line.

To characterize the electrophysiology of the engineered tissue and to perform field potential measurements a custom MEA was designed, characterized and fabricated (FIGS. 5A-C). The MEA was aligned and bonded to the MPS, and the electrophysiology of the cardiac tissue was characterized using five microelectrodes (FIG. 5, panels B, C).

FIG. 5. (A) Two cardiac devices bonded to the custom MEA. (B) Optical microscopy image of a cardiac MPS bonded onto the custom MEA revealing the five microelectrodes inside the cell channel. (C) MEA tracing of hiPSC-CMs recorded with the first generation of the custom MEA featuring the typical field potential shapes.

As an alternative to MEAs, a computational motion tracking method capable of performing high throughput analysis was developed. The computational motion tracking method analyzed the beating motion of cardiac tissue based on simple bright field movies (FIGS. 6A-C).

Figure 6:
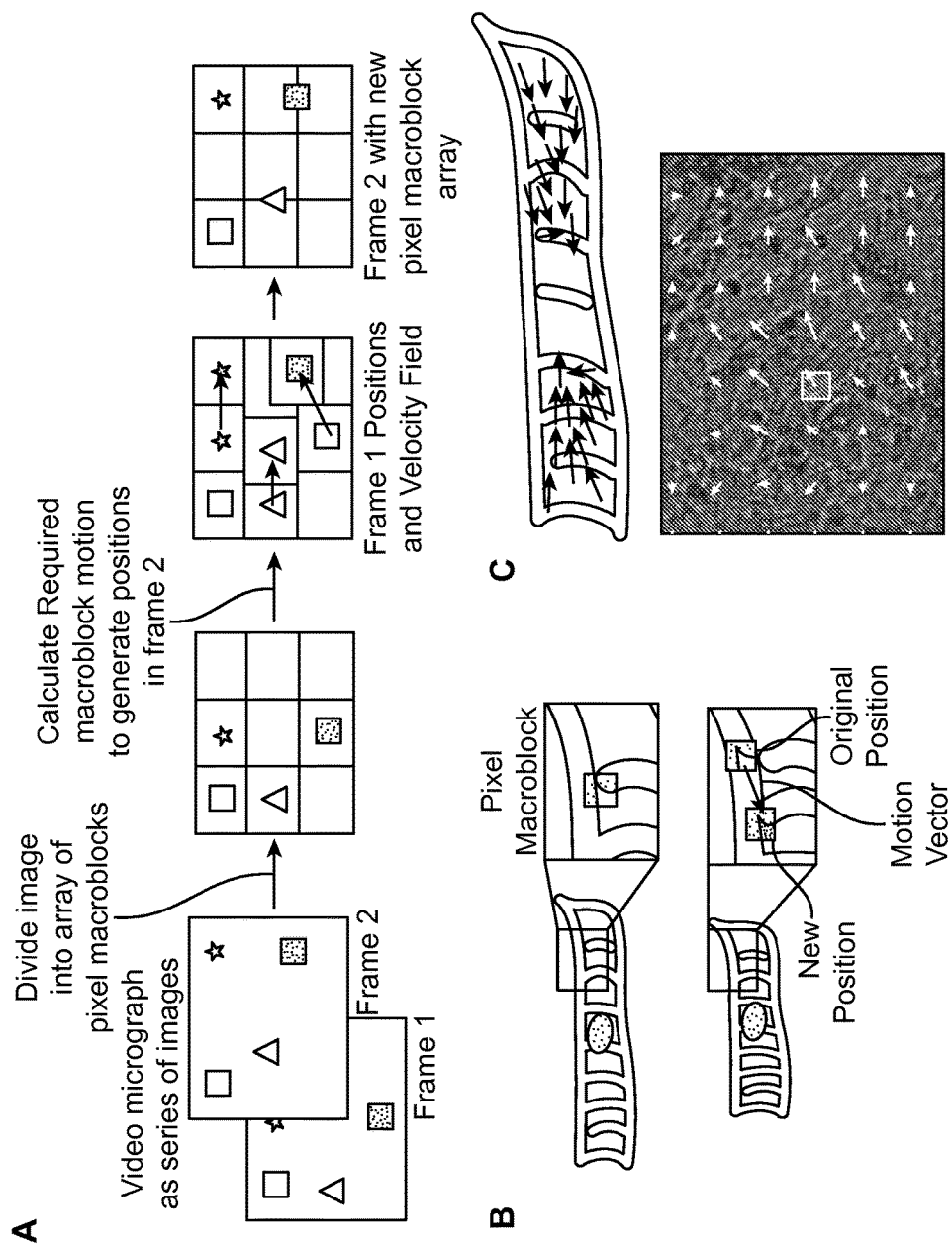
FIGS. 6A-C depict a method of tracking motion in a high throughput analysis of beating cardiac tissue, according to an embodiment of the present disclosure.

FIG. 6. (A) A block-matching optical flow algorithm estimates motion in arbitrary sets of images. First, a still frame (Frame 1; left) was divided up into a grid of macroblocks. In a subsequent frame (Frame 2; right), the position of the macroblock was identified, and the motion vector (red) connecting the original and new macroblock positions was calculated (center). (B) Schematic depicting application of block-matching to cardiomyocyte motion analysis. (C) By tracking movement of all macroblocks from Frame 1 to Frame 2, a field of vectors indicating motion velocity was generated, as shown in schematic form (top) and within a beating sheet of hiPSC-CMs (bottom).

The method required no advanced infrastructure and allowed for a parallelized, high-throughput analysis, which was non-invasive and very cost efficient. The software was optimized with a graphical user interface for user-friendly operation. Motion tracking and calcium reporter cell lines were combined, which allowed for simultaneous monitoring of mechanical motion and electrophysiological activity. In principle, the motion tracking method also allows for the quantification of contraction forces from beating velocities by assuming average elasticity values of the tissue. The software for motion detection was particularly useful for cardiac contractility. To directly measure forces, the cell chamber of the device was additionally equipped with PDMS pillars (FIG. 2, panels A, B). The different features of the real-time cardiac MPS functional measurements motifs are compared in the table provided in FIG. 12.

Healthy hiPSC-CM derived cardiac tissue had physiologically relevant mean field potential duration (~400 ms) and beat rates (60 beats/min). LQTS hiPSC-CM-derived cardiac tissue had physiologically relevant mean field potential duration (~600 ms) and beat rates (60 beats/min). Thus both healthy and LQTS microtissues had physiologically relevant electrophysiology, beat rates, and were amenable to drug screening studies.

Example 3: Validation of the Response of the Cardiac MPS to Physiological Agents The effects of various physiological agents that have known clinical effects in the cardiac MPS were validated and tested, and good concordance with clinical observations was demonstrated (table provided in FIG. 13). Drugs from classes that target a different physiological effect (i.e. ion channel, stimulant) were chosen, and the $IC_{50}$ or $EC_{50}$ values were determined. The MPS was easy to use and produced consistent and reproducible data. The pharmacological studies on the MPS showed $IC_{50}$ or $EC_{50}$ values that were more consistent with the data on tissue scale references compared to cellular scale studies. Thus, the MPS, when compared to two-dimensional studies and animal models, is a better predictor of clinical cardiology. One drug, Verapamil is discussed in detail below as a model example, and results from other drugs are tabulated below (FIG. 13) with data presented in FIGS. 7A-C and 8A-B.

Figure 7:
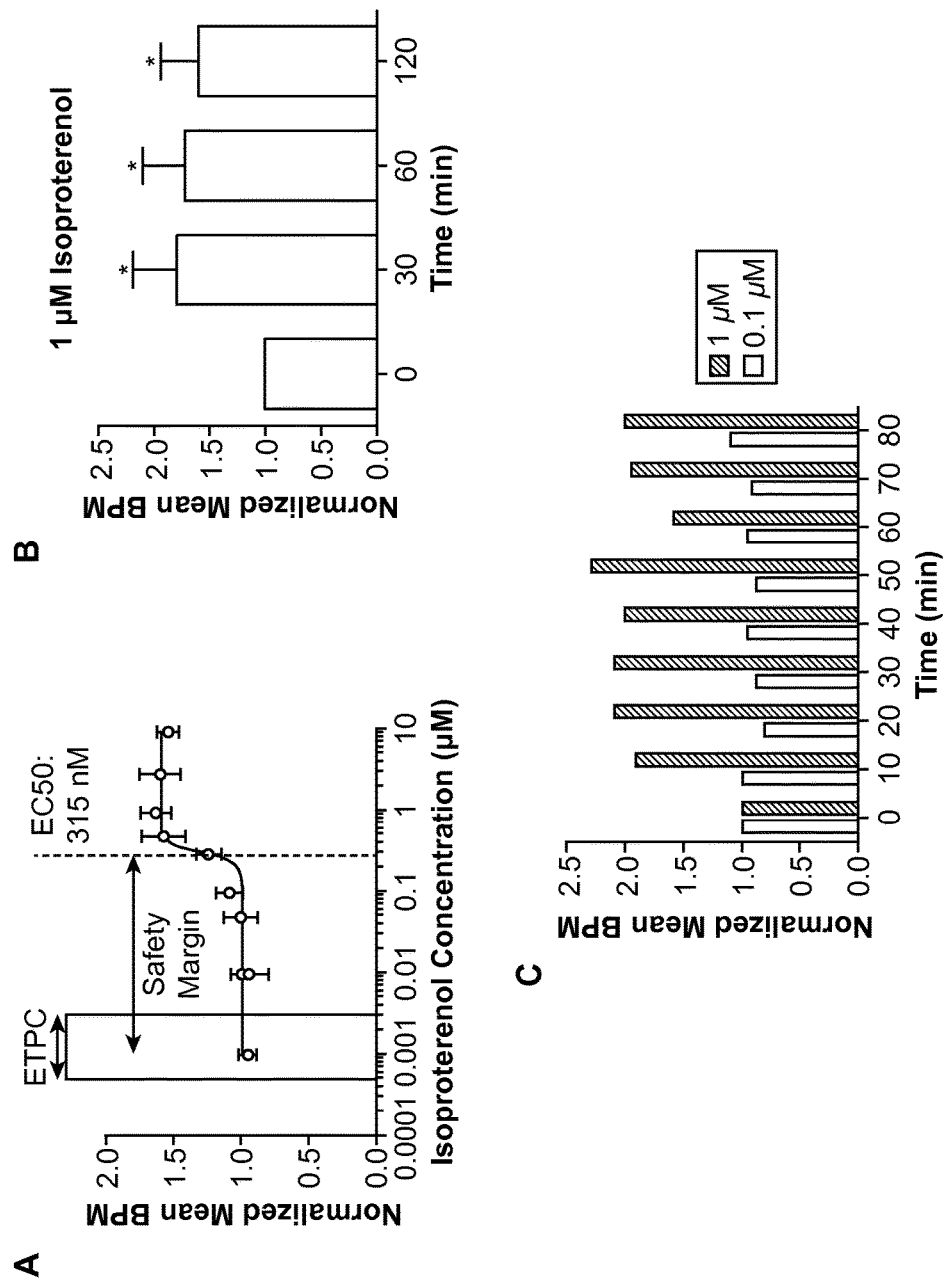
FIGS. 7A-C depict the response of hiPSC-CM derived cardiac tissue to isoproterenol, according to an embodiment of the present disclosure.

FIG. 7. Isoproterenol causes a dose-dependent increase in beats per minute (BPM). (A) Concentration dependent increase on absolute beating with an $EC_{50}$ value of 315 nM. (B) Time dependent effect of 1 µM Isoproterenol (ISO) on bpm. * p<0.05 vs baseline. Interestingly, the $EC_{50}$ for the effect of ISO on beat rate is higher than the $EC_{50}$ for the effect of ISO adult human slice contractility of 100-200 nM. (C) LQT3 hiPSC-CM derived cardiac tissue in the MPS shows a dose dependent response to Isoproterenol. After a 10 min exposure to 1 µM Isoproterenol the beat frequency approximately doubled, no effect was observed at 100 nM concentration.

Figure 8:
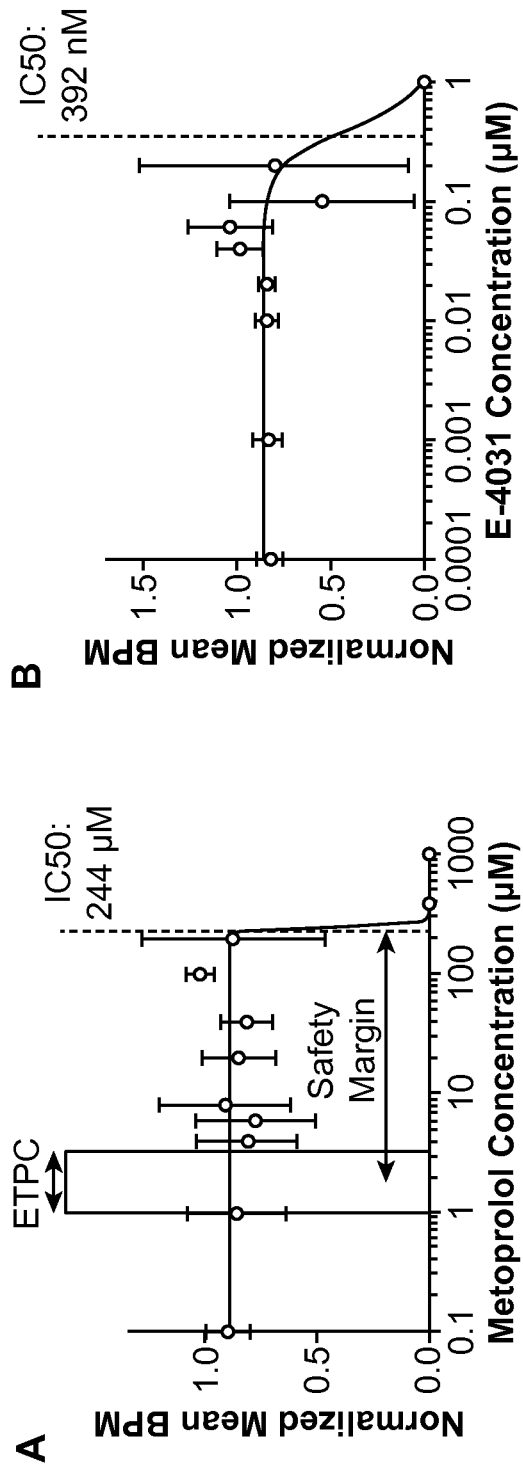
FIGS. 8A and 8B depict the response of hiPSC-CM derived cardiac tissue to a β blocker and a $K^+$ channel blocker, according to an embodiment of the present disclosure.

FIG. 8. β blocker and $K^+$ channel blocker cause a dose dependent decrease of beat rate. (A) Metoprolol $IC_{50}$=244 µM, (B) E-4031 $IC_{50}$=392 nM. No excitation-threshold plasma concentration (ETPC) is highlighted for E-4031 as the drug is used solely for research purposes and only one clinical trial was conducted.

The cardiac MPS was capable of generating low cost and high-throughput results that compare to the industry gold standard of myocardial tissue slices, which are not scalable.

Verapamil: Conventional methods to test the $IC_{50}$ value of Verapamil would indicate it would cause arrhythmias in humans. However, even though conventional drug safety tests suggest the $IC_{50}$ value of Verapamil would cause arrhythmias in humans, few arrhythmias are observed clinically. The $IC_{50}$ value for Verapamil in the MPS with WTC CMs was determined (FIG. 9A-B).

Figure 9:
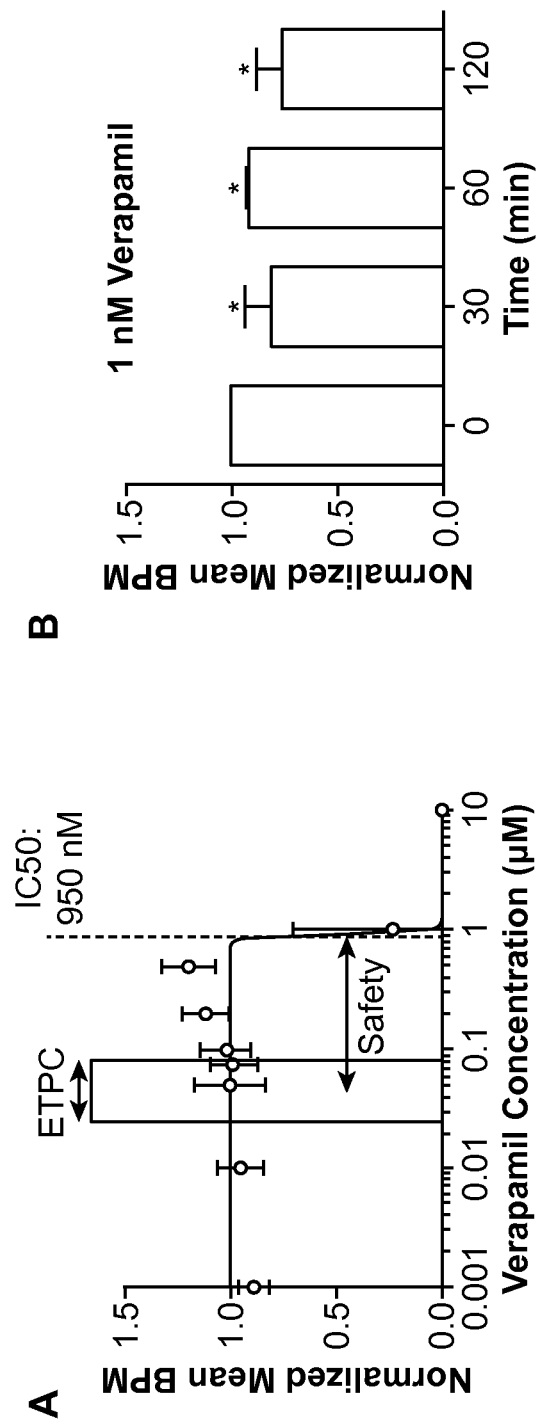
FIGS. 9A and 9B depict the response of cardiac MPS to verapamil, according to an embodiment of the present disclosure.

FIG. 9. The cardiac MPS was exposed to Verapamil causing a dose-dependent decrease in beats per minute (BPM). (A) Verapamil abolished spontaneous beating at high doses with an $IC_{50}$ value of 950 nM. (B) Time dependent effect of Verapamil on BMP (1 nM). * p<0.05 vs baseline.

The Estimated Therapeutic unbound Plasma Concentration ($ETPC_{unbound}$) is 25-81 nM for Verapamil. Based on conventional drug screening assays the $IC_{50}$/ETPC (mean) is approximately 1.7, clearly indicating the spread is too low to allow for safe use. However, clinical observations indicate a very low number of arrhythmias in patients. One major reason for the difference is that conventional tests cannot account for species differences and lack of complex ion channel interactions. In addition, there is a heavy reliance on hERG ion channel without assessment of the full spectrum of human ion channels in many of these tests. This is especially important regarding Verapamil, as it affects multiple ion channels—it blocks both blocks $Ca^{2+}$ and hERG ion channels, and the effects occur at different concentrations.

Since human cells were used in the MPS, the issues with ion channels were alleviated, but more importantly, the chip promoted the alignment of the CMs, coordinated their beating more consistently with less variance, and the fluidics design delivered a precise concentration of the drug continuously during the entire drug testing period. The MPS gave both a high and clinically safe margin of 21× $IC_{50}$/ETPC (mean $ETPC_{unbound}$ was used 45 nM) (table provided in FIG. 13). Therefore the MPS gave more clinically relevant data due to the enhanced maturity of the cells and the aforementioned other attributes of the system.

Multiple drug exposures (3) were conducted on the same device to demonstrate the repeated use and repeatability of the MPS (FIGS. 10A-C). Excellent repeatability was observed upon exposure to multiple drugs that had opposite effects on cardiac beat rate.

Figure 10:
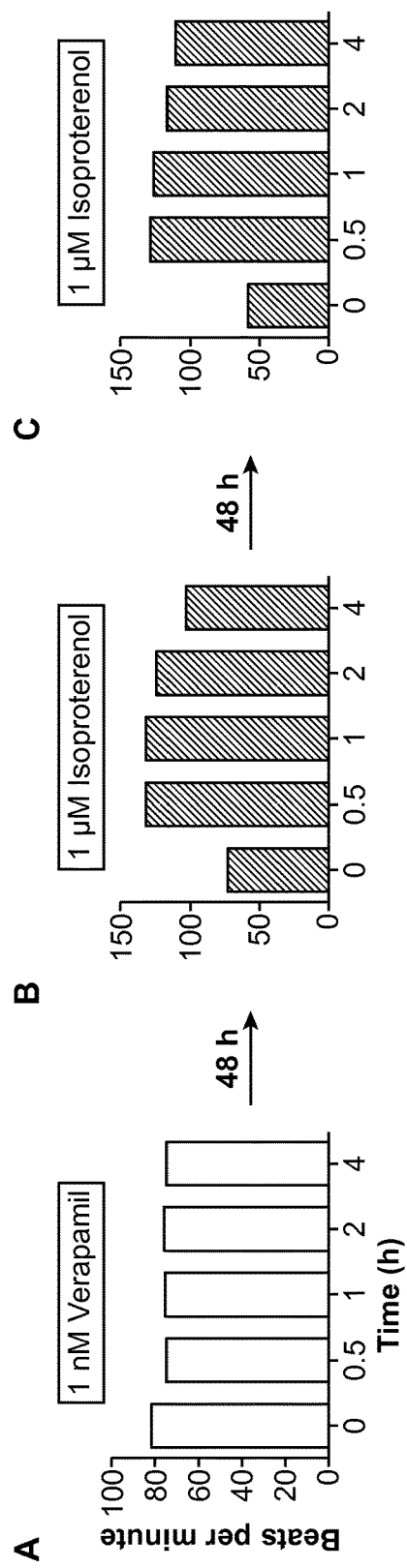
FIGS. 10A-C depict the response of cardiac MPS to multiple exposures of verapamil and isoproterenol, according to an embodiment of the present disclosure.

FIG. 10. Multiple drug exposures on the same device. (A) Exposure to 1 nM Verapamil decreased the beat rate. (B, C) Subsequent exposure to 1 µM Isoproterenol increased the beat rate. Before each exposure the microtissue was washed with drug tree media for at least 48 hours.

Example 4: Use of the Mechanocardiogram to Measure Cardiac Cell Activity

The Mechanocardiogram (MCG) is a noninvasive procedure for recording the beat rate and the rhythm of the heart. It is an alternative method for diagnosing various cardiac abnormalities, for example, ischemic heart disease, arrhythmias (irregular heart beat), tachycardia (fast heartbeat), bradycardia (slow heartbeat), myocardial infarction (heart attack), and certain congenital heart conditions. The PDMS pillars in the cell channel serve as sensors for the beat rate and the heart rhythm. As a proof of principle, it was shown that wild type cells beating in the cell channel deform the micropillars. This deflection, when analyzed yields an alternative method to measure the beat rate of the cardiac tissue as shown in FIGS. 14A-C. Using computational methods the pillar displacement is measured in X and Y direction and the resultant displacement is computed by these two values. The peaks of X, Y, and resultant displacement shown in FIGS. 14A-C correspond to the beating of the 3d microtissue. FIGS. 14A-C depict use of a device of the instant disclosure as a mechanocardiogram to measure heart rate and heart rhythm. FIG. 14A: Displacement of the pillar in the X-direction. FIG. 14B: Displacement of the pillar in the Y-direction. FIG. 14C: resultant displacement. The x-axis represents pillar displacement in pixels and the y-axis represents the acquisition rate (10 frames per second for a total of 30 seconds).

Figure 15:
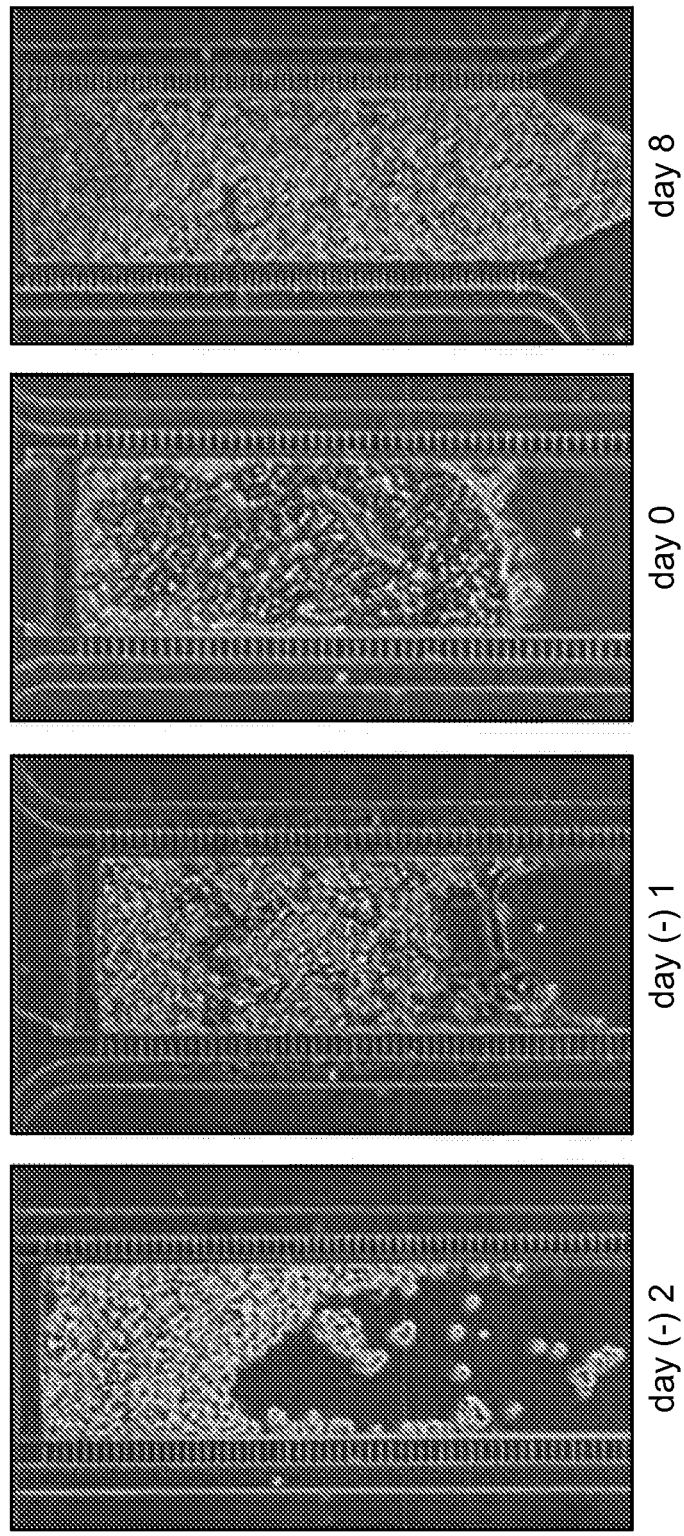
FIG. 15 depicts differentiation of human induced pluripotent stem cells into various lineages in a device of the present disclosure.

There is an urgent need in pharmaceutical industry to effectively and efficiently screen potential drug compounds during early stages to assess both effectiveness and toxicity. The present physiologically functioning integrated cardiac systems can be used for drug compound on a subset of patients. This is relevant to determining pharmacokinetics and pharmacodynamics for patients, such as patients with rare genetic disorders. The present device can be used for on-chip differentiation of hiPSCs into various lineages as shown in FIG. 15. FIG. 15 depicts on-chip differentiation, in which hiPSCs were seeded and observed for multiple days. Furthermore, the MCG can be used as alternative to for diagnosing various cardiac abnormalities.

Example 5: Device Fabrication

Where the device is made of an elastomeric material (polydimethyl siloxane (PDMS)), a rigid mold can be formed. The fabrication of the mold in SU-8 was performed in two steps: (1) fabrication of the endothelial like barriers and spacing platform; (2) fabrication of the media channels and cell channel including the features (pillars and weir). An example of the microfabrication process is described in detail below.

Four-inch silicon wafers were subjected to piranha clean (a mixture of 70% sulfuric acid and 30% hydrogen peroxide by volume), followed by a 30 min dehydration bake at 120° C. The wafers were then spin-coated with 2 µm thick SU8-2001 (MicroChem Corp, MA, USA) and subsequently soft-baked on a hot plate at 95° C. for 60 s to evaporate residual solvents from the photoresist film. Next, the substrates were patterned via conventional UV photolithography. A chrome photomask with the endothelial like barriers and the spacing platform was formed for the first level of lithography using a MP80+ laser pattern generator. Su-8 was exposed at 104 mJ/cm$^2$ on a mask aligner (Karl Suss MA-6). After exposure, the wafers were postbaked on a hot plate at 95° C. for 60 s and developed for 100 s with SU-8 developer (MicroChem Corp, MA, USA). Next, the wafers were hard baked at 175° C. for 15 minutes.

The next fabrication process for patterning the cell channel and media channel involved a second level of lithography. For this, the wafers were coated with 35 μm SU8-3035 (MicroChem Corp, MA, USA) and soft-baked on a hot plate at 70° C. for 2 min followed by 13 min bake at 100° C. The resist was then exposed at 250 mJ/cm$^2$ on a mask aligner and postexposure baked at 70° C. for 1 min followed by a 5 min bake at 100° C. The resist was developed for 5 minutes with SU-8 developer (MicroChem Corp. MA) followed by a hard bake at 175° C. for 30 minutes.

PDMS Molding, Surface Chemistry, and Cell Culture

The wafers were silanized in AMST Molecular Vapor Deposition System (MVD100) with vapor phase Tridecafluoro-1,1,2,2-Tetrahydrooctyl-1-Trichlorosilane (Gelest, Inc) for 30 min to facilitate the release of the elastomer from the wafer post curing. PDMS (Sylgard 184, Dow Corning) was mixed thoroughly with its curing agent in a 10:1 ratio and degassed in a vacuum chamber for 30 min to remove trapped air. It was poured over the SU-8 mold and cured at 65° C. for 12 h. The PDMS was then peeled off the mold, fluidic ports in the PDMS devices were made with a 1 mm biopsy punch (Harris Uni-Core). For bonding both PDMS and glass coverslips were oxidized in oxygen plasma for 20 s (60 W, 10 atm cm$^3$/min, and 20 millitorr).

To promote cellular adhesion, the substrates were coated with 20 μg/ml fibronectin (Invitrogen) in phosphate buffered saline (PBS) for 1 h at 37° C. and 5% $CO_2$ prior to plating.

Predifferentiated beating hiPSC-CMs were dissociated and seeded on devices for subsequent analysis. HiPSC-CMs were re-suspended in EB-20 media and plated on the device using gravity flow. To reduce fibroblast proliferation, the medium was switched to RPMI/B27 48 hours post-seeding. Cells were monitored for multiple days and tested for viability as shown in FIG. 16. FIG. 16 (upper panel) is a bright-field image of cells in the device 3 days post loading. FIG. 16 (lower panel) depicts live/dead staining of cells 3 days post loading. The scale bar (upper panel) is 200 μm.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A device for culturing cells, the device comprising:
    a cell culture channel; and
    two media channels disposed on either side of the cell culture channel;
    wherein the media channels are in fluid communication with the cell culture channel; and
    wherein the cell culture channel comprises a weir that extends across the width of the cell culture channel and is adapted for loading a plurality of cells into the cell culture channel at a low pressure.

2. The device according to claim 1, wherein the cell culture channel comprises a sensor that is adapted to collect data from a plurality of cells in the cell culture channel.

3. The device according to claim 2, wherein the sensor comprises a mechanosensing pillar.

4. The device according to claim 3, wherein;
    a) the mechanosensing pillar has a spring constant that ranges from 0.005 μN/μm to 1 μN/μm; and/or
    b) the mechanosensing pillar is adapted to form a gap that ranges in height from 1 μm to 5 μm between a bottom surface of the cell culture channel and a bottom surface of the mechanosensing pillar; and/or
    c) the mechanosensing pillar is configured to measure a force created by a contraction of one or more cells that are cultured in the device.

5. The device according to claim 2, wherein the mechanosensing pillar has a circular cross-sectional shape or a rectangular cross-sectional shape.

6. The device according to claim 2, wherein the sensor comprises an electrode.

7. The device according to claim 6, wherein the electrode is disposed on a bottom surface of the cell culture channel.

8. The device according to claim 6, wherein the electrode comprises indium tin oxide, gold, platinum black, or platinum.

9. The device according to claim 6, wherein the electrode has a rectangular shape and has an edge length that ranges from 20 μm to 300 μm, or wherein the electrode has a circular shape and has a diameter that ranges from 20 μm to 300 μm.

10. The device according to claim 2, wherein the sensor comprises a multi-electrode array (MEA) chip that comprises a plurality of electrodes.

11. The device according to claim 10, wherein the MEA chip comprises 2 to 10 measurement electrodes, and/or wherein the MEA chip comprises 1 or 2 reference electrodes.

12. The device according to claim 11, wherein the measurement electrodes are disposed on a bottom surface of the cell culture channel.

13. The device according to claim 11, wherein the reference electrodes are disposed on a bottom surface of the cell culture channel, or wherein the reference electrodes are located in an outlet of the cell culture channel.

14. The device according to claim 11, wherein the measurement electrodes have a rectangular shape and have an edge length that ranges from 20 μm to 50 μm, or wherein the measurement electrodes have a circular shape and have a diameter that ranges from 20 μm to 50 μm.

15. The device according to claim 11, wherein the reference electrodes have a rectangular shape and have an edge length that ranges from 50 μm to 300 μm, or wherein the reference electrodes have a circular shape and have a diameter that ranges from 50 μm to 300 μm.

16. The device according to any one of the previous claims, wherein:
   a) the cell culture channel has a width that ranges from 30 μm to 200 μm; and/or
   b) the cell culture channel has a height that ranges from 30 μm to 200 μm; and/or
   c) the cell culture channel has a length that ranges from 0.6 mm to 5 mm; and/or
   d) the media channels have a width that ranges from 20 μm to 100 μm; and/or
   e) the media channels have a height that ranges from 30 μm to 200 μm.

17. The device according to claim 1, wherein the cell culture channel is connected to the media channels by a plurality of microchannels that are adapted to prevent cell migration between the cell culture channel and the media channels.

18. The device according to claim 17 to, wherein:
   a) the microchannels have a height that ranges from 0.1 μm to 5 μm; and/or
   b) the microchannels have a width that ranges from 0.1 μm to 5 μm; and/or
   c) the microchannels have a length of 10 μm; and/or
   d) the microchannels have a pitch that ranges from 2 μm to 20 μm.

19. The device according to claim 1, wherein the cell culture channel comprises an alignment component adapted to align the cell culture channel and the media channels with the microchannels.

20. The device according to claim 19, wherein the alignment component comprises an overhang having a height that ranges from 0.1 μm to 5 μm and a depth that ranges from 1 μm to 5 μm.

21. The device according to claim 1, wherein the cell culture channel comprises an outlet, and wherein the weir is configured to partially block the outlet.

22. The device according to claim 1, wherein the weir is adapted to form a gap that ranges in height from 1 μm to 5 μm between a bottom surface of the cell culture channel and a bottom surface of the weir.

23. The device according to claim 1, further comprising a plurality of ports that are fluidly connected to one or more portions of the device.

24. A system for culturing cells, the system comprising:
   a device according to claim 1; and
   a computational motion capturing component that is configured to image a plurality of cells that are cultured in the device.

25. A method for culturing cells, the method comprising:
   introducing a plurality of cells into the cell culture channel of a cell culture device according to claim 1;
   introducing a cell culture medium into the media channels of the device; and
   maintaining the device under suitable cell culture conditions.

26. A method for evaluating a plurality of cells in vitro, the method comprising:
   introducing a plurality of cells into the cell culture channel of a cell culture device according to claim 1;
   introducing a cell culture medium into the media channels of the device;
   maintaining the device under suitable cell culture conditions; and
   measuring a characteristic of the cells.

27. A method for identifying a candidate agent that modulates a characteristic of a plurality of cells, the method comprising:
   introducing a plurality of cells into the cell culture channel of a cell culture device according to claim 1;
   introducing a cell culture medium into the media channels of the device;
   contacting the cells with the candidate agent;
   maintaining the device under suitable cell culture conditions;
   measuring a characteristic of the cells; and
   identifying whether the candidate agent modulates the characteristic of the cells,
   wherein a change in the characteristic of the cells in the presence of the candidate agent compared to a characteristic of the cells in the absence of the candidate agent indicates that the candidate agent has use in modulating the characteristic of the cells.

28. A method of evaluating an effect of an agent on a plurality of cells, the method comprising:
   introducing a plurality of cells into the cell culture channel of a cell culture device according to claim 1;
   introducing a cell culture medium into the media channels of the device;
   contacting the cells with the agent;
   maintaining the device under suitable cell culture conditions;
   measuring a characteristic of the cells; and
   evaluating the effect of the agent on the cells,
   wherein a change in the characteristic of the cells in the presence of the agent compared to a characteristic of the cells in the absence of the agent indicates that the agent modulates the characteristic of the cells.

* * * * *

SEQUENCE LISTING

```
<160> NUMBER OF SEQ ID NOS: 1

<210> SEQ ID NO 1
<211> LENGTH: 448
<212> TYPE: PRT
<213> ORGANISM: Artificial Sequence
<220> FEATURE:
<223> OTHER INFORMATION: Calcium indicator (GECI) protein
<220> FEATURE:
<221> NAME/KEY: misc_feature
<222> LOCATION: (222)..(222)
<223> OTHER INFORMATION: Xaa can be any naturally occurring amino acid

<400> SEQUENCE: 1
```

Met Gly Ser His His His His His His Gly Met Ala Ser Met Thr Gly
1               5                   10                  15

Gly Gln Gln Met Gly Arg Asp Leu Tyr Asp Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

-continued

```
Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Xaa Val Gln
            210                 215                 220

Cys Phe Ser Arg Tyr Pro Asp His Met Lys Gln His Asp Phe Phe Lys
225                 230                 235                 240

Ser Ala Met Pro Glu Gly Tyr Ile Gln Glu Arg Thr Ile Phe Phe Lys
                245                 250                 255

Asp Asp Gly Asn Tyr Lys Thr Arg Ala Glu Val Lys Phe Glu Gly Asp
                260                 265                 270

Thr Leu Val Asn Arg Ile Glu Leu Lys Gly Ile Asp Phe Lys Glu Asp
            275                 280                 285

Gly Asn Ile Leu Gly His Lys Leu Glu Tyr Asn Leu Pro Asp Gln Leu
            290                 295                 300

Thr Glu Glu Gln Ile Ala Glu Phe Lys Glu Ala Phe Ser Leu Phe Asp
305                 310                 315                 320

Lys Asp Gly Asp Gly Thr Ile Thr Thr Lys Glu Leu Gly Thr Val Met
                325                 330                 335

Arg Ser Leu Gly Gln Asn Pro Thr Glu Ala Glu Leu Gln Asp Met Ile
            340                 345                 350

Asn Glu Val Asp Ala Asp Gly Asp Gly Thr Ile Asp Phe Pro Glu Phe
            355                 360                 365

Leu Thr Met Met Ala Arg Lys Gly Ser Tyr Arg Asp Thr Glu Glu Glu
    370                 375                 380

Ile Arg Glu Ala Phe Gly Val Phe Asp Lys Asp Gly Asn Gly Tyr Ile
385                 390                 395                 400

Ser Ala Ala Glu Leu Arg His Val Met Thr Asn Leu Gly Glu Lys Leu
                405                 410                 415

Thr Asp Glu Glu Val Asp Glu Met Ile Arg Glu Ala Asp Ile Asp Gly
            420                 425                 430

Asp Gly Gln Val Asn Tyr Glu Glu Phe Val Gln Met Met Thr Ala Lys
            435                 440                 445
```